United States Patent
Li et al.

(10) Patent No.: US 10,461,261 B2
(45) Date of Patent: Oct. 29, 2019

(54) COMPOUND, LIGHT EMITTING MATERIAL, AND ORGANIC LIGHT EMITTING DEVICE

(71) Applicants: KYUSHU UNIVERSITY, NATIONAL UNIVERSITY CORPORATION, Fukuoka-shi, Fukuoka (JP); NIPPON STEEL Chemical & Material Co., Ltd., Tokyo (JP)

(72) Inventors: Bo Li, Fukuoka (JP); Akihiro Orita, Okayama (JP); Hiroshi Miyazaki, Kitakyushu (JP); Junzo Otera, Okayama (JP); Hiroko Nomura, Fukuoka (JP); Chihaya Adachi, Fukuoka (JP)

(73) Assignees: KYUSHU UNIVERSITY, NATIONAL UNIVERSITY CORPORATION, Fukuoka (JP); NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 0 days.

(21) Appl. No.: 14/905,019

(22) PCT Filed: Jun. 23, 2014

(86) PCT No.: PCT/JP2014/066501
§ 371 (c)(1),
(2) Date: Jan. 14, 2016

(87) PCT Pub. No.: WO2015/008580
PCT Pub. Date: Jan. 22, 2015

(65) Prior Publication Data
US 2016/0164000 A1    Jun. 9, 2016

(30) Foreign Application Priority Data

Jul. 16, 2013 (JP) ................. 2013-147714

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/82* (2013.01); *C07D 209/86* (2013.01);
(Continued)

(58) Field of Classification Search
None
See application file for complete search history.

(56) References Cited

U.S. PATENT DOCUMENTS 9,082,986 B2    7/2015  Kato et al.
2013/0234119 A1*  9/2013  Mizuki ............ H01L 51/0072
257/40

(Continued)

FOREIGN PATENT DOCUMENTS

TW    201326121 A1    7/2013
WO    2012165256 A1   12/2012

(Continued)

OTHER PUBLICATIONS

Li etal., Dicarbazolyldicyanobenzens as Thermally Activated Delayed fluorence Emitters: Effect of Substitution Position on the photoluminescent and Electronluminescent Properties, Chem. Lett., 2014, 43, 319-321.*

(Continued)

*Primary Examiner* — Gregory D Clark
(74) *Attorney, Agent, or Firm* — Browdy and Neimark, PLLC

(57) ABSTRACT

A compound represented by A-D-A is useful as a light. emitting material used in an organic electroluminescent device and others.

(Continued)

US 10,461,261 B2
Page 2

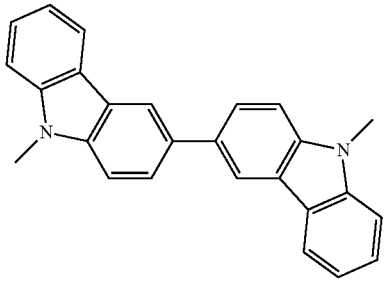

D

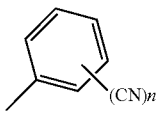

A

10 Claims, 3 Drawing Sheets

(51) Int. Cl.
C07D 209/82 (2006.01)
C09K 11/06 (2006.01)
C07D 209/86 (2006.01)

(52) U.S. Cl.
CPC ...... *C09K 11/06* (2013.01); *C09K 2211/1007* (2013.01); *C09K 2211/1029* (2013.01); *H01L 51/006* (2013.01); *H01L 51/5012* (2013.01); *H01L 51/5016* (2013.01)

(56) References Cited

U.S. PATENT DOCUMENTS

2014/0001446 A1* 1/2014 Mizuki ............... C07D 209/86
257/40
2014/0110692 A1 4/2014 Kato et al.

FOREIGN PATENT DOCUMENTS

WO 2013084881 A1 6/2013
WO 2013084885 A1 6/2013

OTHER PUBLICATIONS

Li et al., Dicarbazolyldicyanobenzenes as Thermally Activated Delayed Fluorescence Emitters: Effect of Substitution Position on Photoluminescent and Electroluminescent Properties, 2014, Chem. Lett. 43, 319-321 (Year: 2014).*
International Search Report, dated Sep. 9, 2014. in corresponding application No. PCT/JP2014/066501.
Ambrose, et al "Electrochemical and Spectroscopic Properties of Cation Radicals." Department of Chemistry, University of Georgia 122 (7) 876-894 (1975).
Herbich, et al "Phoshorescent Intramolecular Charge Transfer Triplet States" Chemical Physics Letters. 262: 633-642 (1996).
Kapturkiewicz et al "Intramolecular Radiative and Radiationless Charge Recombination Processes in Donor-Acceptor Carbazole Derivatives" Journal of Physical Chemistry . 101:2332-2344 (1997).
Kapturkiewicz , et al "Highly efficient electrochemical generation of of fluorescent intramolecular charge-transfer states" Chemical Physics Letters. 275 : 355-362 (1997).
Cazeau-Dubroca, et al, "TICT Fluorescence in Rigid Matrices: A-Delayed Fluorescence" Chemical Physics Letters. 124:2 (1986).
Ishimatsu, et al "Solvent Effect on Thermally Activated Delayed Fluorescence by 1,2,3,5-Tetrakis (carbazol-9-yl)-4,6-dicyanobenzene" The journal of Physical Chemistry. 117:5607-5612 (2013).
Uoyama et al "Highly efficient organic light-emitting diodes from delayed fluorescence" Nature 492: 234-238 (2012).
International preliminary report on patentability, dated Jan. 1, 2016. in corresponding application No. PCT/JP2014/066501.
European search report from European application No. 14827119.0 dated Feb. 10, 2017.
Office Action issued in corresponding Chinese Patent Application No. 201480040513.3, dated May 4, 2017, with English translation.
Office Action issued in corresponding Chinese Patent Application No. 201480040513.3, dated Jan. 15, 2018, with English Machine Translation.
Office Action issued in corresponding Taiwanese Patent Application No. 103121629, dated Mar. 14, 2018, with English Translation.
Office Action issued in corresponding European Patent Application No. 14827119.0, dated Feb. 19, 2019.
Office Action issued in corresponding Korean Patent Application No. 10-2016-7003768, dated May 20, 2019, with English Machine Translation.

* cited by examiner

COMPOUND, LIGHT EMITTING MATERIAL, AND ORGANIC LIGHT EMITTING DEVICE

TECHNICAL FIELD

The present invention relates to a compound that is useful as a light emitting material, and an organic light emitting device using the same.

BACKGROUND ART

An organic light emitting device, such as an organic electroluminescent device (organic EL device), has been actively studied for enhancing the light emission efficiency thereof. In particular, various studies for enhancing the light emitting efficiency have been made by newly developing and combining an electron transporting material, a hole transporting material, a light emitting material and the like constituting an organic electroluminescent device. There are studies relating to an organic electroluminescent device utilizing a compound containing a bicarbazole structure, and some proposals have been made hitherto.

For example, Patent Document 1 describes the use of the compound having the following bicarbazole structure as a hole transporting material. There is stated that the use of the compound as a hole transporting material may provide an organic electroluminescent device that is capable of being driven at a low voltage and has a prolonged service life. Patent Document 1 describes the compound containing a bicarbazole structure, but does not describe a structure containing a 3,3'-bicarbazole skeleton that has cyanebenzenes substituted on the two nitrogen atoms thereof. Furthermore, the compound is used as a hole transporting material, and the use of the compound as a light emitting material and the usefulness thereof are not described.

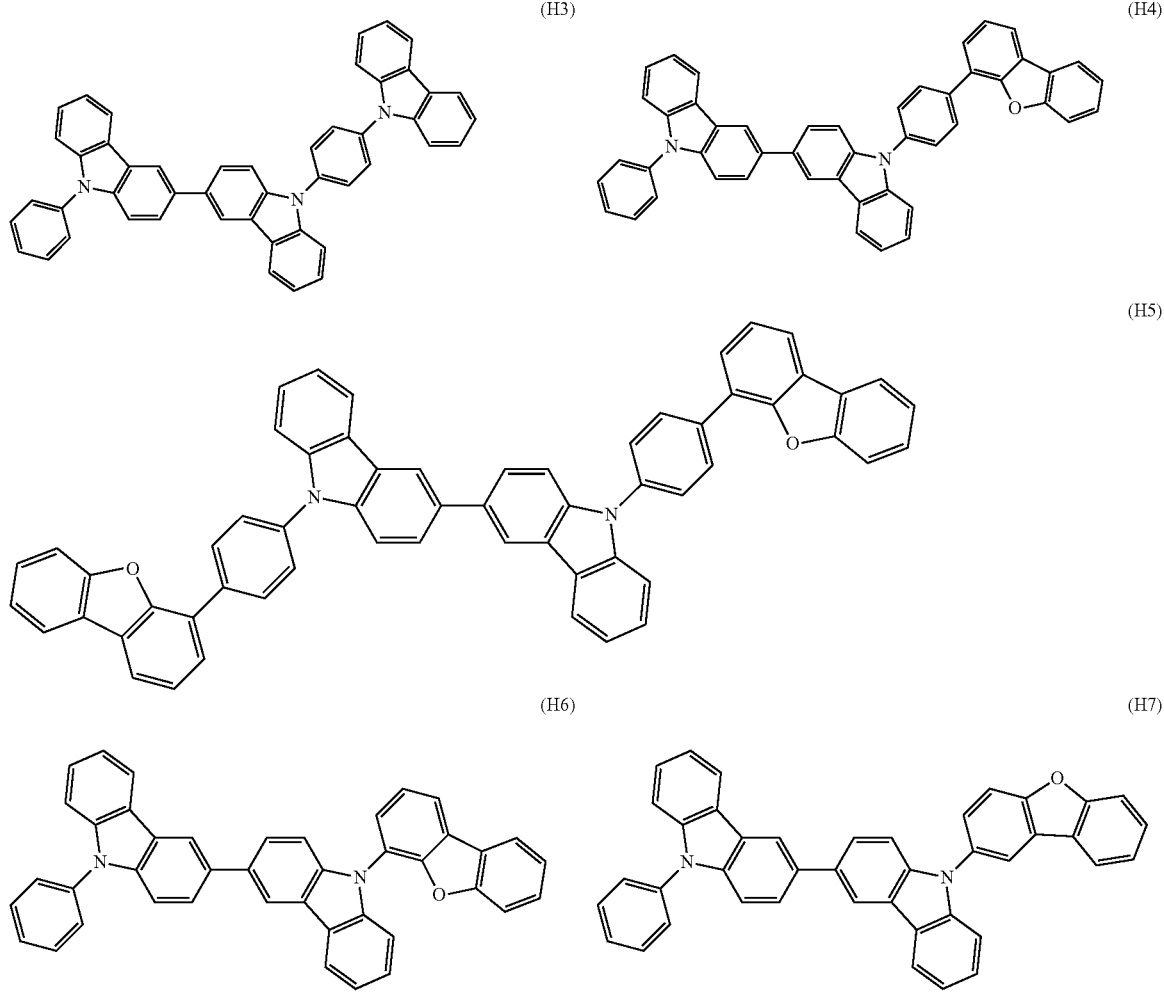

Patent Document 2 describes the use of the compound represented by the following general formula as a host material of a light emitting layer. It is stated that in the general formula, $A^1$ and $A^2$ each represent an aromatic hydrocarbon group or a heterocyclic group, $A^3$ represents a monocyclic hydrocarbon group or a monocyclic heterocyclic group, m represents an integer of from 0 to 3, $X^1$ to $X^8$ and $Y^1$ to $Y^8$ each represent N or $CR^a$, and $R^a$ represents a hydrogen atom, an aromatic hydrocarbon group, a heterocyclic group, an alkyl group, a silyl is group or a halogen atom. Examples or compounds that are included in the general formula include compounds having a 3,3'-bicarbazole skeleton, but there is no description of data showing the usefulness of the compound represented by the general formula as a light emitting material.

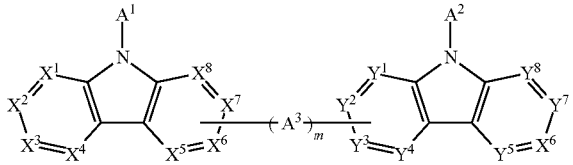

CITATION LIST

Patent Documents

Patent Document 1: WO 2012/165256
Patent Document 2: WO 2013/084881

SUMMARY OF INVENTION

Technical Problem

As described above, the proposals have been made for the application of the compound containing a bicarbazole structure in an organic electroluminescent device. However, there has been no specific investigation result about the compound having a structure containing a 3,3'-bicarbazole skeleton that has cyanobenzenes substituted on the two nitrogen atoms thereof. Accordingly, it is significantly difficult to expect accurately the properties exhibited by the compound having the structure.

Various schemes have been made for enhancing the light emission efficiency of the organic electroluminescent device. For enhancing the light emission efficiency of the organic electroluminescent device, the development of a novel compound capable of being used as a light emitting material has been considered, but it is still unknown what type of structure should be selected for improving the light emission efficiency. In this point of view, Patent Document 1 proposes the use of the compound containing a bicarbazole structure as a hole transporting material of an organic electroluminescent device, and Patent Document 2 proposes the use of the compound as a host material. However, there has been no investigation on the use of the compound as a light emitting material, and the usefulness thereof has not yet been suggested.

In consideration of the related art problems, the present inventors have made investigations on the use of a compound having a bicarbazole structure as a light emitting material. Furthermore, the inventors have made investigations on the object of providing a compound having a high light emission efficiency among the compounds having a bicarbazole structure.

Solution to Problem

As a result of earnest investigations for achieving the objects, the inventors have succeeded synthesis of a compound having a 3,3'-bicarbazole skeleton that has cyanobenzenes substituted on the two nitrogen atoms thereof, and firstly clarified that the compound is useful as a light emitting material. The inventors also have found that the compound is useful as a delayed fluorescent material, and an organic light emitting device having a high light emission efficiency can be provided inexpensively. Based on the knowledge, the inventors have provided the following inventions as measures for solving the problems.

(1) A compound represented by the following general formula (1):

A-D-A            General Formula (1)

wherein in the general formula (1), D represents a divalent group containing a structure represented by the following formula:

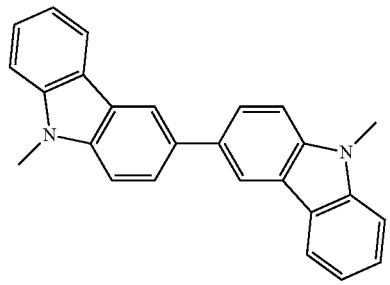

wherein a hydrogen atom in the structure may be substituted by a substituent, and A represents a group having a structure represented by the following formula:

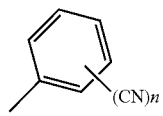

wherein a hydrogen atom in the structure may be substituted by a substituent except for a cyano group, and n represents an integer of from 1 to 5.

(2) The compound according to the item (1), wherein the two groups represented by A have the same structure.

(3) The compound according to the item (1) or (2), wherein the compound is represented by the following general formula (2):

General Formula (2)

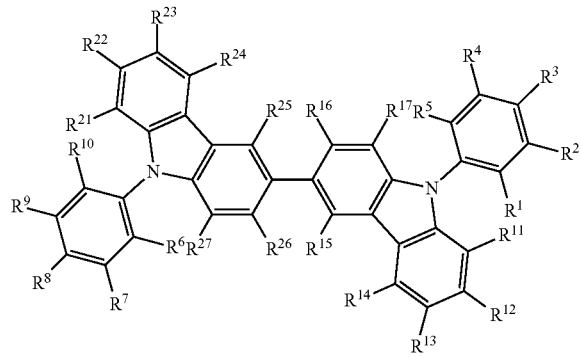

wherein in the general formula (2), $R^1$ to $R^5$ each independently represent a hydrogen atom or a substituent, provided that at least one thereof represents a cyano group; $R^6$ to $R^{10}$ each independently represent a hydrogen atom or a substituent, provided that at least one thereof represents a cyano group; and $R^{11}$ to $R^{17}$ and $R^{21}$ to $R^{27}$ each independently represent a hydrogen atom or a substituent.

(4) The compound according to the item (3), wherein in the general formula (2), at least two of $R^1$ to $R^5$ each represent a cyano group, and at least two of $R^6$ to $R^{10}$ each represent a cyano group.

(5) The compound according to the item (3) or (4), wherein in the general formula (2), $R^1$, $R^5$, $R^6$ and $R^{10}$ each represent a cyano group.

(6) The compound according to any one of the items (3) to (5), wherein in the general formula (2), $R^2$, $R^4$, $R^7$ and $R^9$ each represent a cyano group.

(7) The compound according to any one of the items (3) to (6), wherein in the general formula (2), $R^1$ to $R^5$ and $R^6$ to $R^{10}$ except for one representing a cyano group each represent a hydrogen atom or a substituted or unsubstituted alkyl group having from 1 to 10 carbon atoms, and $R^{11}$ to $R^{17}$ and $R^{21}$ to $R^{27}$ each represent a hydrogen atom or a substituted or unsubstituted alkyl group having from 1 to 10 carbon atoms.

(8) The compound according to any one of the items (3) to (7), wherein in the general formula (2), $R^1$ to $R^5$ and $R^6$ to $R^{10}$ except for one representing a cyano group each represent a hydrogen atom, and $R^{11}$ to $R^{17}$ and $R^{21}$ to $R^{27}$ each represent a hydrogen atom.

(9) A light emitting material containing the compound according to any one of the items (1) to (8).

(10) A delayed fluorescent material having a structure represented by the following general formula (1):

A-D-A                General Formula (1)

wherein in the general formula (1) D represents a divalent group containing a structure represented by the following formula:

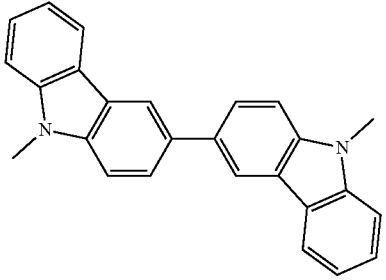

wherein a hydrogen atom in the structure may be substituted by a substituent, and A represents a group having a structure represented by the following formula:

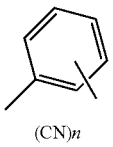

(CN)n wherein a hydrogen atom in the structure maybe substituted by a substituent except for a cyano group, and n represents an integer of from 1 to 5.

(11) An organic light emitting device containing a substrate having thereon a light emitting layer containing the light emitting material according to the item (9).

(12) The organic light emitting device according to the item (11), wherein the organic light emitting device emits delayed fluorescent light.

(13) The organic light emitting device according to the item (11) or (12), wherein the organic light emitting device is an organic electroluminescent device.

Advantageous Effects of invention

The compound containing at bicarbazole structure of the invention is useful as a light emitting material. The compound of the invention includes one that emits delayed fluorescent light. The organic light emitting device using the compound of the invention as a light emitting material is capable of achieving a high light emission efficiency.

DESCRIPTION OF EMBODIMENTS

Figure 1:
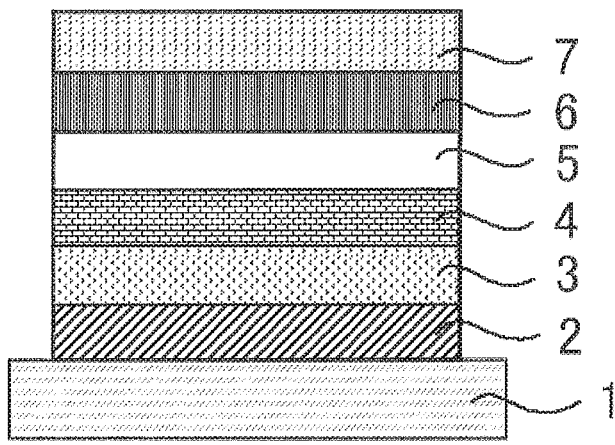
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H deuterium (D)).

Compound Represented by General Formula (1)

The compound of the invention has the structure represented by the following general formula (1):

A-D-A                General Formula (1)

In the general formula (1), D represents a divalent group containing a structure represented by the following formula:

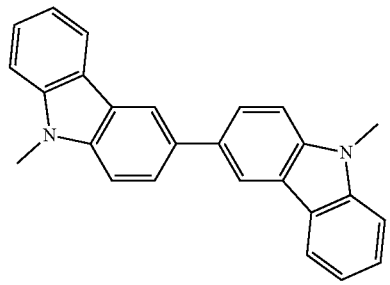

A hydrogen atom present in the structure may be substituted by a substituent. The number of the substituent is not particularly limited, and the substituent may not be present. In the case where two or more substituents are present, the substituents may be the same as or different from each other.

Examples of the substituent include a hydroxyl group, a halogen atom, an alkyl group having from 1 to 20 carbon atoms, an alkoxy group having from 1 to 20 carbon atoms, an alkylthio group having from 1 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, a haloalkyl group having from 1 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, and a trialkylsilylalkynyl group having from 5 to 20 carbon atoms. In these specific examples, the substituent that is capable of being further substituted with a substituent may be substituted. More preferred examples of the substituent include a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, and a substituted or unsubstituted heteroaryl group having from 3 to 40 carbon atoms. Further preferred examples of the substituent include a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

The alkyl group may be linear, branched or cyclic, and more preferably has from 1 to 6 carbon atoms, and specific examples thereof include a methyl group, an ethyl group, a propyl group, a butyl group, a tert-butyl group, a pentyl group, a hexyl group, and an isopropyl group. The alkoxy group may be linear, branched or cyclic, and more preferably has from 1 to 6 carbon atoms, and specific examples thereof include a methoxy group, an ethoxy group, a propoxy group, a butoxy group, a tert-butoxy group, a pentyloxy group, a hexyloxy group, and an isopropoxy group. The aryl group that may be used as the substituent may be a monocyclic ring or a condensed ring, and specific examples thereof include a phenyl group and a naphthyl group. The heteroaryl group may be a monocyclic ring or a condensed ring, and specific examples thereof include a pyridyl group, a pyridazyl group, a pyrimidyl group, a triazyl group, a triazolyl group, and a benzotriazolyl group. The heteroaryl group may be a group that is bonded through the hetero atom or a group that is bonded through the carbon atom constituting the heteroaryl ring.

In the general formula (1), A represents a group having a structure represented by the following formula:

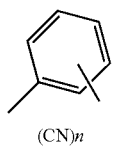

(CN)n

A hydrogen atom in the structure may be substituted by a substituent except for a cyano group. The number of the substituent is not particularly limited, and the substituent may not be present. In the case where two or more substituents are present, the substituents may be the same as or different from each other.

Examples of the substituent, by which the hydrogen atom in the structure is substituted, include a hydroxyl group, a halogen atom, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an aryl-substituted amino group having from 12 to 40 carbon atoms, an acyl group having fro 2 to 20 carbon atoms, an aryl group having from 6 to 40 carbon atoms, a heteroaryl group having from 3 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a substituted or unsubstituted group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted dialkylamino group having from 2 to 10 carbon atoms, a substituted or unsubstituted diarylamino group having from 12 to 40 carbon atoms, and a substituted or unsubstituted carbazolyl group having from 12 to 40 carbon atoms. Further preferred examples of the substituent include a fluorine atom, a chlorine atom, a substituted or unsubstituted alkyl group having from to 10 carbon atoms, a substituted or unsubstituted alkoxy group having from 1 to 10 carbon atoms, a substituted or unsubstituted dialkylamino group having from 2 to 10 carbon atoms, a substituted or unsubstituted diarylamino group having from 12 to 40 carbon atoms, a substituted or unsubstituted aryl group having from 6 to 15 carbon atoms, and a substituted or unsubstituted heteroaryl group having from 3 to 12 carbon atoms.

In the general formula (1), the two groups represented by A may be the same as or different from each other, and are preferably the same as each other. In the case where the two groups represented by A are the same as each other, the entire molecule is preferably line-symmetric or point-symmetric.

An ordinary light emitting material has an A-D structure formed of A functioning as an acceptor and D functioning as a donor. On the other hand, the compound represented by the general formula (1) has the A-D-A structure having two groups of A each functioning as an acceptor bonded to one group of D functioning as a donor. There may be generally a possibility that two or more groups of A annihilate the acceptor function of each other, and thereby the molecule fails to function as a light emitting material effectively. However, it has been found that a light emitting material that has a high light emission efficiency and exhibits excellent effects may be provided by carefully selecting and combining the groups of A and D according to the invention. It is considered this is because the spreads of the HOMO and the LUMO are controlled on the molecular level, so as to satisfy the conditions that are favorable as a light emitting material.

The compound represented by the general formula (1) is preferably a compound having a structure represented by the following general formula (2):

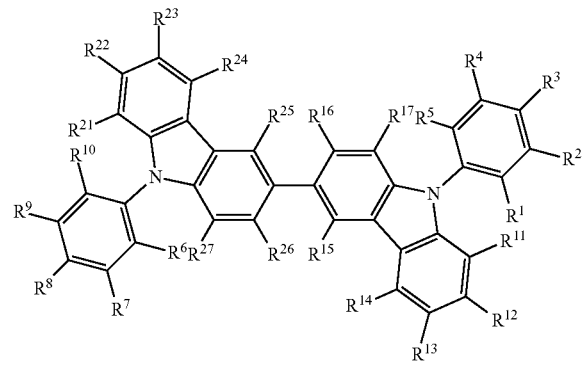

General Formula (2)

In the general formula (2), $R^1$ to $R^5$ each independently represent a hydrogen atom or a substituent, provided that at least one thereof represents a cyano group; $R^6$ to $R^{10}$ each independently represent a hydrogen atom or a substituent, provided that at least one thereof represents a cyano group; and $R^{11}$ to $R^{17}$ and $R^{21}$ to $R^{27}$ each independently represent a hydrogen atom or a substituent.

In $R^1$ to $R^5$ and $R^6$ to $R^{10}$, examples of the combination of the one position having a cyano group substituted thereon in each of $R^1$ to $R^5$ and $R^6$ to $R^{10}$ include the case where $R^5$ and $R^6$ each represent a cyano group, the case where $R^4$ and $R^7$ each represent a cyano group, and the case where $R^3$ and $R^8$ each represent a cyano group.

In the general formula (2), it is preferred that at least two of $R^1$ to $R^5$ each represent a cyano group, and at least two of $R^6$ to $R^{10}$ each represent a cyano group. It is particularly preferred that two or three of $R^1$ to $R^5$ each represent a cyano group, and two or three of $R^6$ to $R^{10}$ each represent a cyano group.

In $R^1$ to $R^5$ and $R^6$ to $R^{10}$, examples of the combination of the two positions each having a cyano group substituted thereon in each of $R^1$ to $R^5$ and $R^6$ to $R^{10}$ include the case where $R^4$, $R^5$, $R^6$ and $R^7$ each represent a cyano group, the case where $R^3$, $R^4$, $R^7$ and $R^8$ each represent a cyano group, the case where $R^1$, $R^3$, $R^6$ and $R^8$ each represent a cyano group, the case where $R^1$, $R^5$, $R^6$ and $R^{10}$ each represent a cyano group, the case where $R^2$, $R^4$, $R^7$ and $R^9$ each represent a cyano group, and the case where $R^2$, $R^5$, $R^7$ and $R^{10}$ each represent a cyano group.

In $R^1$ to $R^5$ and $R^5$ to $R^{10}$, examples of the combination of the three positions each having a cyano group substituted thereon in each of $R^1$ to $R^5$ and $R^6$ to $R^{10}$ include the case where $R^1$, $R^3$, $R^5$, $R^6$, $R^8$ and $R^{10}$ each represent a cyano group, the case where $R^3$, $R^4$, $R^5$, $R^6$, $R^7$ and $R^8$ each represent a cyano group, and the case where $R^2$, $R^3$, $R^4$, $R^8$ and $R^9$ each represent a cyano group.

In the general formula (2), it is particularly preferred that $R^1$, $R^5$, $R^6$ and $R^{10}$ each represent a cyano group, or $R^2$, $R^4$, $R^7$ and $R^9$ each represent a cyano group. The light emission efficiency may be enhanced by the cyano groups at the ortho positions with respect to the bonding positions of the two nitrogen atoms of the 3,3'-bicarbazole skeleton and the cyanobenzenes.

In the general formula (2), $R^5$ and $R^6$ to $R^{10}$ except for one representing a cyano group each preferably represent a hydrogen atom or a substituted or unsubstituted alkyl group having from 1 to 10 carbon atoms, and $R^{11}$ to $R^{17}$ and $R^{21}$ to $R^{27}$ each preferably represent a hydrogen atom or a substituted or unsubstituted alkyl group having from 1 to 10 carbon atoms. Among the cases, $R^1$ to $R^5$ and $R^6$ to $R^{10}$ except for one representing a cyano group each more preferably represent a hydrogen atom, and $R^{11}$ to $R^{17}$ and $R^{21}$ to $R^{27}$ each more preferably represent a hydrogen atom. The general formula (2) having such a structure may further enhance the light emission efficiency.

Specific examples of the compound represented by the general formula (1) shown below. However, the compound represented by the general formula (1) capable of being used in the invention is not construed as being limited to the specific examples.

1

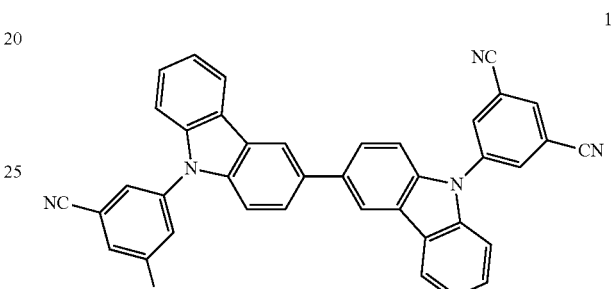

2

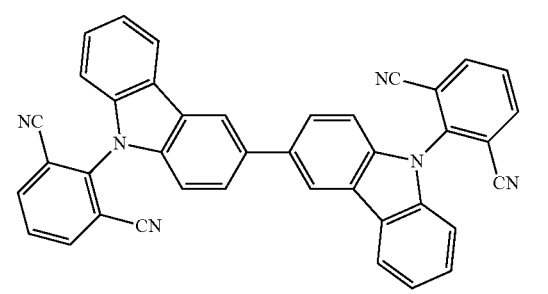

3

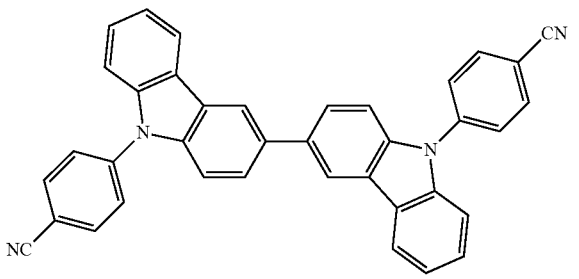

4

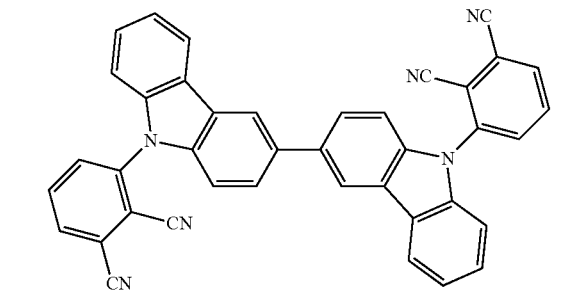

-continued

5
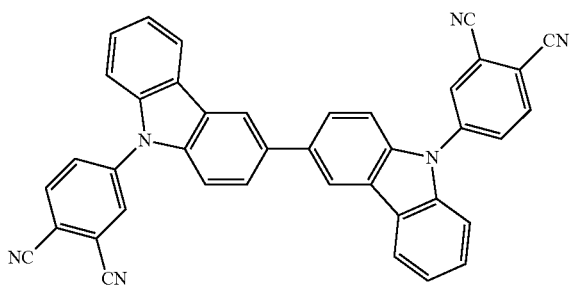

6
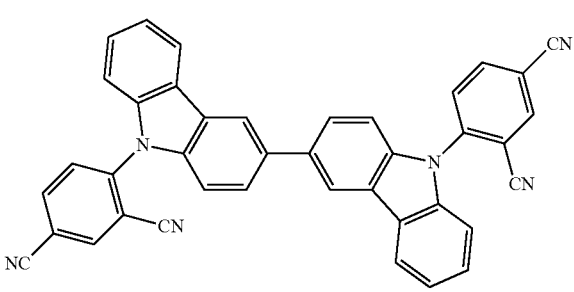

7
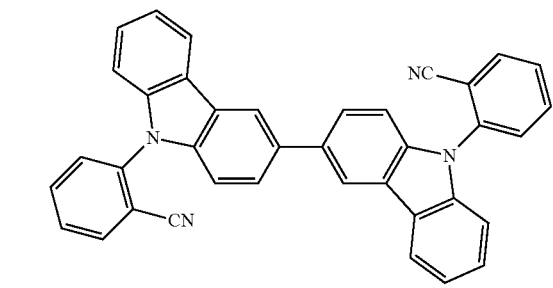

8
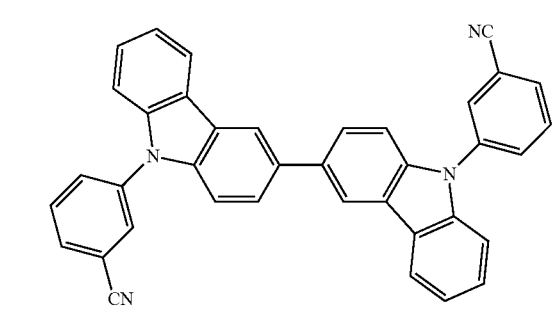

9
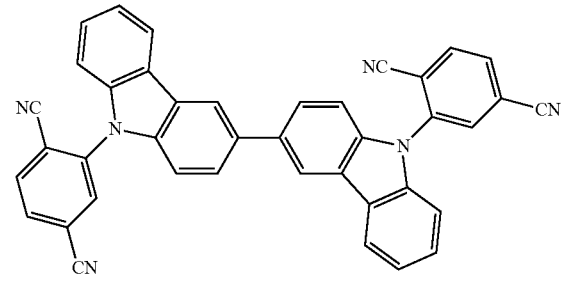

-continued

10
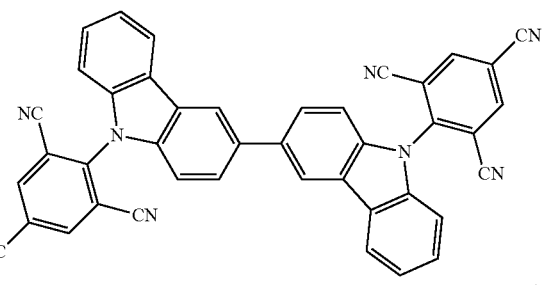

11
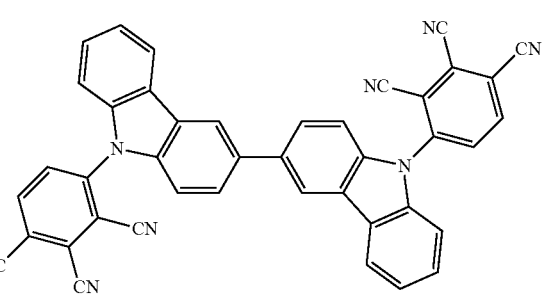

12
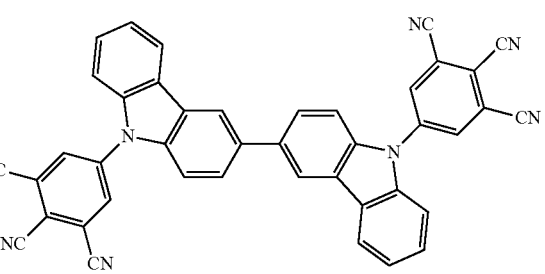

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light emitting material.

For example, it may be considered that a polymerizable group is introduced in advance to the structure represented by the general formula (1), and a polymer obtained by polymerizing the polymerizable group is used as a light emitting material. Specifically, it may be considered that a monomer that has a polymerizable functional group at any of A and D in the general formula (1) is prepared, and is homopolymerized or copolymerized with another monomer to prepare a polymer containing repeating units, and the polymer is used as a light emitting material. In alternative, it may be considered that the compounds represented by the general formula (1) are reacted to form a dimer or a trimer, and the dimer or the trimer is used as a light emitting material.

Examples of the polymer having the repeating unit containing the structure represented by the general formula (1) include a polymer containing a structure represented by the following general formula (4) or (5).

General Formula (4)

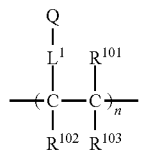

General Formula (5)

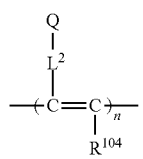

In the general formulae (4) and (5), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by -$X^{11}$-$L^{11}$-, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (4) and (5), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of A and D of the structure of the general formula (1) constituting Q, and $R^1$ to $R^5$ and $R^6$ to $R^{10}$ except for one representing a cyano group, $R^{11}$ to $R^{17}$, and $R^{21}$ to $R^{27}$ of the structure of the general formula (2). Two or more of the linking groups may be boded to one group represented by Q to form a crosslinked structure or a network structure.

Specific examples of the structure of the repeating unit include structures represented by the following formulae (6) to (9).

Formula (6)

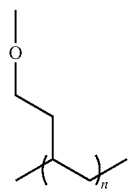

Formula (7)

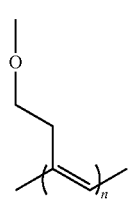

Formula (8)

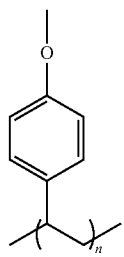

Formula (9)

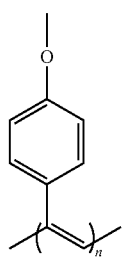

The polymer having the repeating unit containing the structure represented by any of the formulae (6) to (9) may be synthesized in such a manner that a hydroxyl group is introduced to any of A and D in the structure represented by the general formula (1), and the hydroxyl group as a linker is reacted with the following compound Co introduce a polymerizable group thereto, followed by polymerizing the polymerizable group.

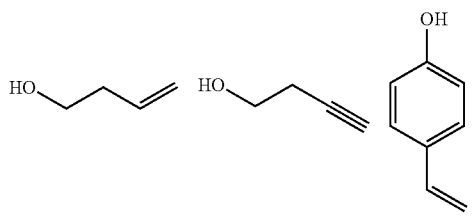

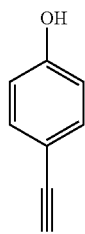

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene. The invention is not limited to the repeating units shown herein.

Synthesis Method of Compound Represented by General Formula (1)

The compound represented by the general formula (1) may be synthesized by combining the known reactions. For example, the compound may be synthesized according to the following scheme.

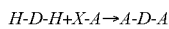

For the descriptions of D and A in the scheme, reference may be made to the corresponding descriptions in the general formula (1). In the scheme, X represents a halogen atom, examples of which include a fluorine atom, a chlorine atom, a bromine atom and an iodine atom, and a chlorine atom, a bromine atom and an iodine atom are preferred.

In the compound represented by the general formula (1), for example, the compound represented by the general formula (2) may be synthesized according to the following scheme. The following scheme shows the synthesis method in the case where $R^1$ and $R^6$, $R^2$ and $R^7$, $R^3$ and $R^8$, $R^4$ and $R^9$, and $R^5$ and $R^{10}$ each are the same as each other.

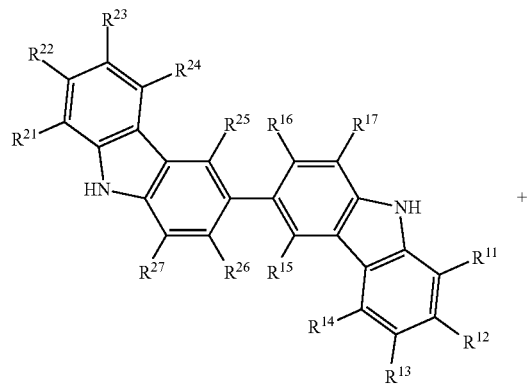

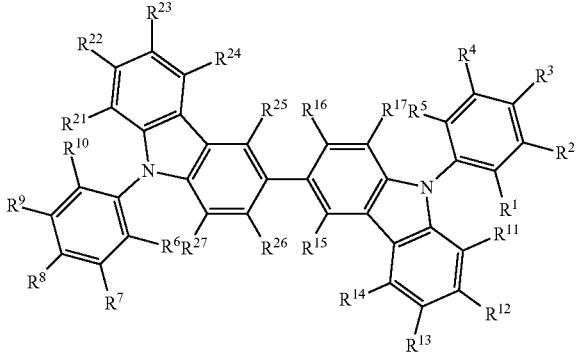

For the descriptions of $R^1$ to $R^5$, $R^6$ to $R^{10}$, $R^{11}$ to $R^{17}$, and $R^{21}$ to $R^{27}$ in the scheme, reference may be made to the corresponding descriptions in the general formula (2). In the scheme, X represents a halogen atom.

The reactions in the aforementioned two schemes each are an application of the known coupling reaction, and the known reaction conditions may be appropriately selected and used. For the details of the reactions, reference may be made to the synthesis examples described later. The compound represented by the general formula (1) may also be synthesized by combining the other known synthesis reactions.

Organic Light Emitting Device

The compound represented by the general formula (1) of the invention is useful as a light emitting material of an organic light emitting device. Accordingly, the compound represented by the general formula (1) of the invention may be effectively used as a light emitting material in a light emitting layer of an organic light emitting device. The compound represented by the general formula (1) includes a delayed fluorescent material emitting delayed fluorescent light. Thus, the invention provides an invention relating to a delayed fluorescent material having the structure represented by the general formula (1), an invention relating to the use of the compound represented by the general formula (1) as the delayed fluorescent material, and an invention relating to a method for emitting delayed fluorescent light with the compound represented by the general formula (1). An organic light emitting device that uses the compound as a light emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light emitting material to form an excited state for the light emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and the transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light emitting material of a light emitting layer may provide an excellent organic light emitting device, such as an organic photoluminescent device (organic PL device) and an organic electroluminescent device (organic EL device). At this time, the compound represented by the general formula (1) of the invention may have a function of assisting light emission of another light emitting material contained in the light emitting layer, i.e., as a so-called assist dopant. Specifically, the compound represented by the general formula (1) of the invention contained in the light emitting layer may have a lowest excited singlet energy level that is between the lowest excited singlet energy level of the host material contained in the light emitting layer and the lowest excited singlet energy level of the another light emitting material contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having a electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from-the anode and the cathode, respectively, are recombined to form excitons, and then the layer emits light. A light emitting material may be solely used as the light emitting layer, but the light emitting layer preferably contains a light emitting material and a host material. The light emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light emitting material are confined in the light emitting material. Accordingly, a host material is preferably used in addition to the light emitting material in the light emitting layer. The host material used may be an organic compound that has excited singlet energy and excited triplet energy, at least one of which is higher than those of the light emitting material of the invention. As a result, the singlet excitons and the triplet excitons generated in the light emitting material of the invention are capable of being confined in the molecules of the light emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light emitting device and the organic electroluminescent device of the invention, the light emission occurs in the light emitting material of the invention contained in the light emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light emitting material contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons sad holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light emitting layer but also in the other layers than the light emitting layer. In this case, the compound represented by the general formula (1) used in the light emitting layer and the compound represented by the general formula (1) used in the other layers than the light emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and it represents an integer of from 3 to 5.

Preferred examples of a compound that may also be used as the host material of the light emitting layer are shown below.

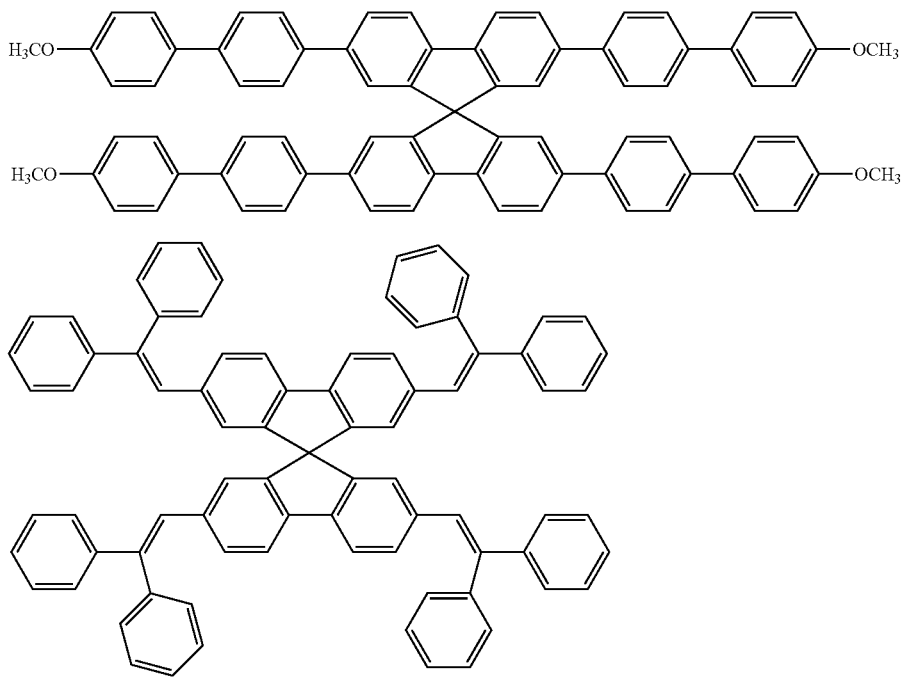

-continued
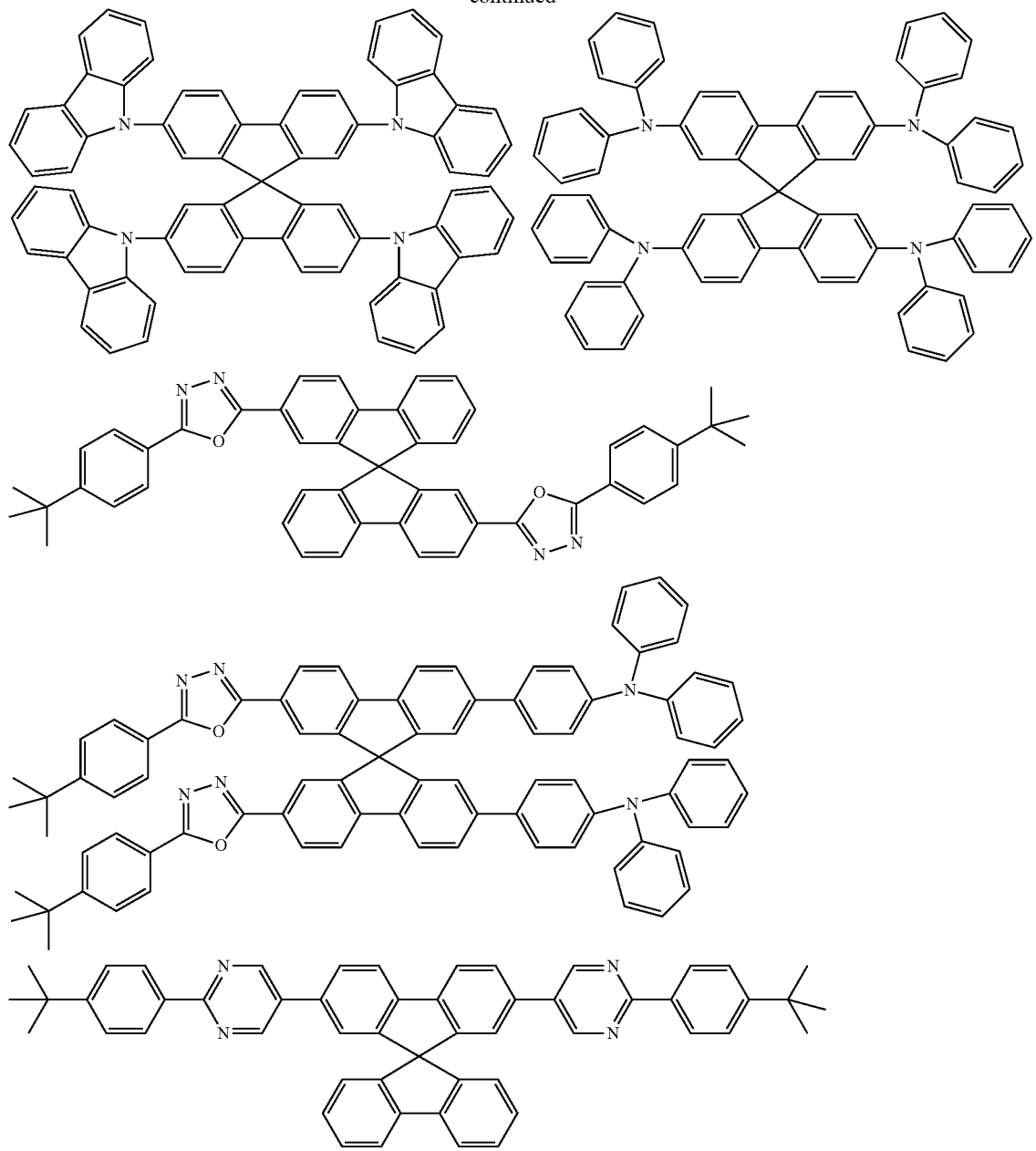
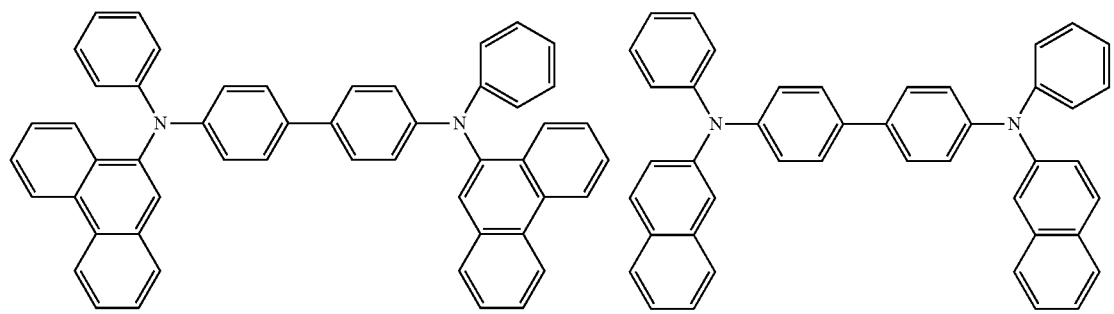

25 26
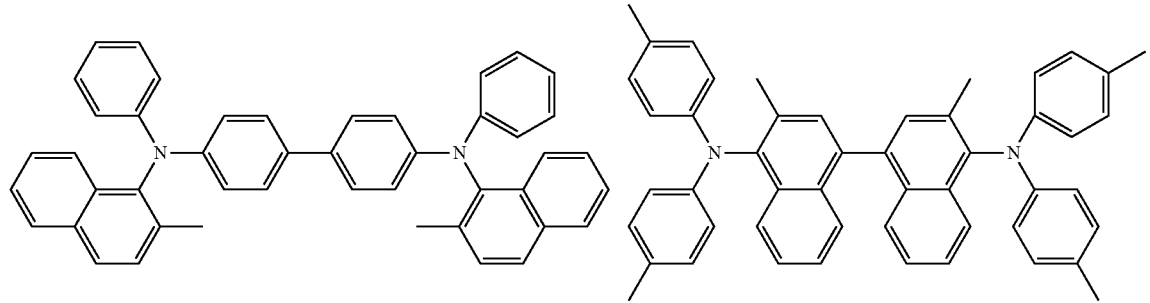
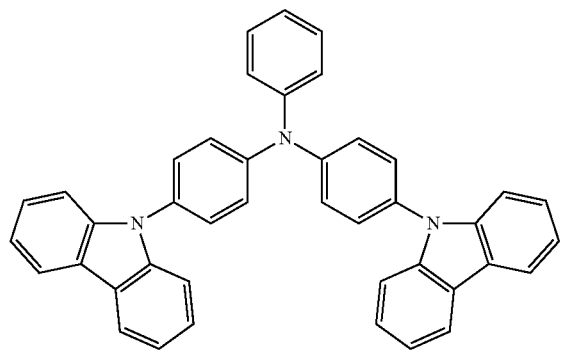
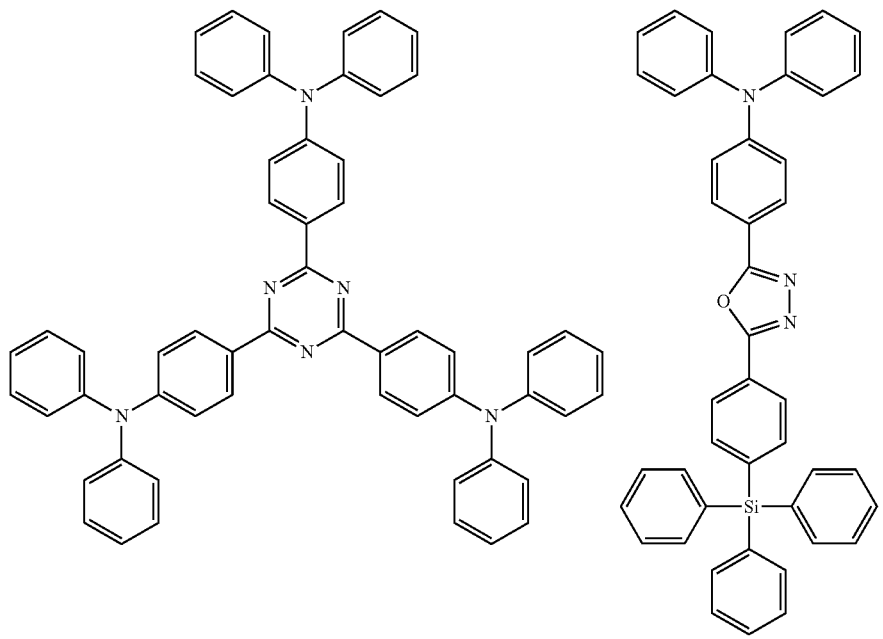

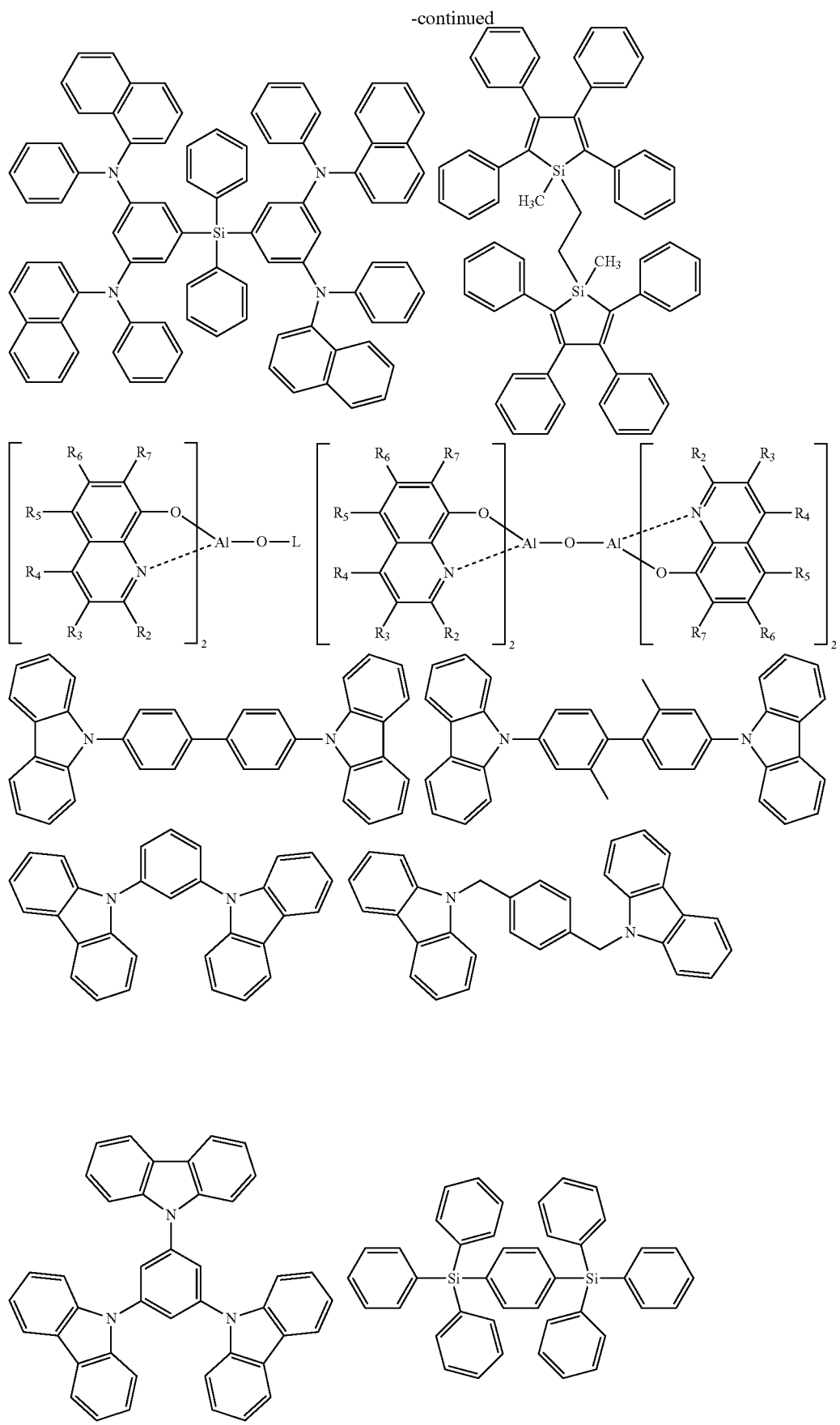

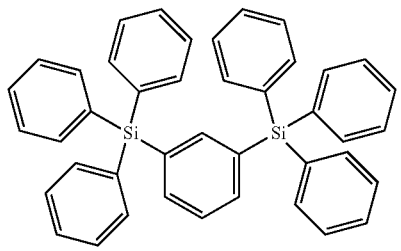
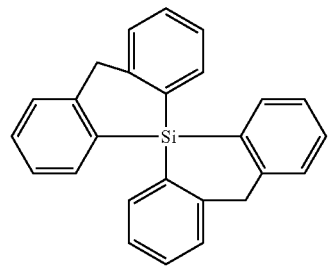
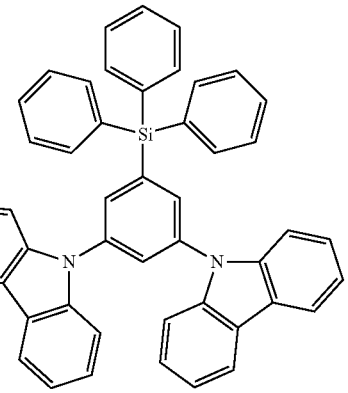
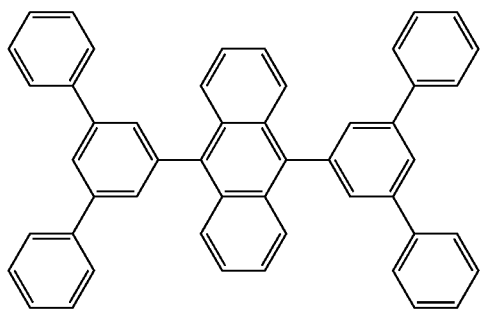
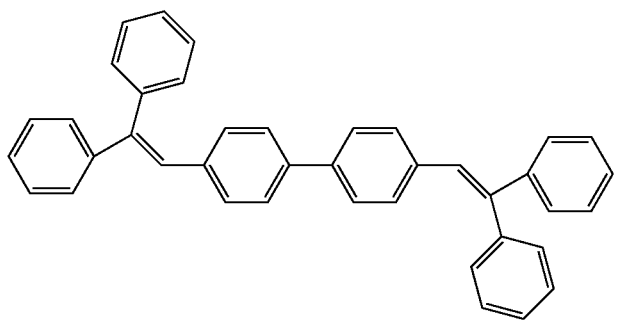
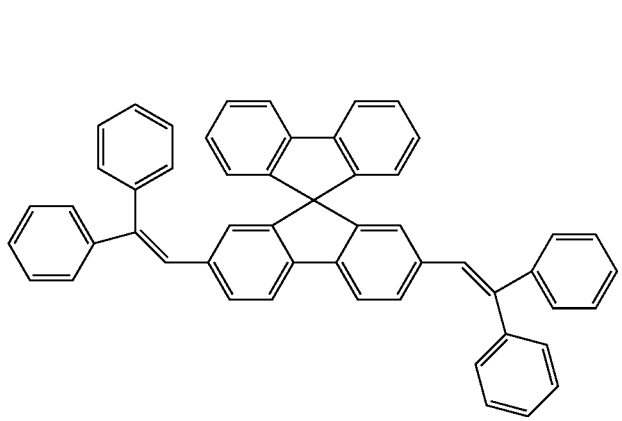
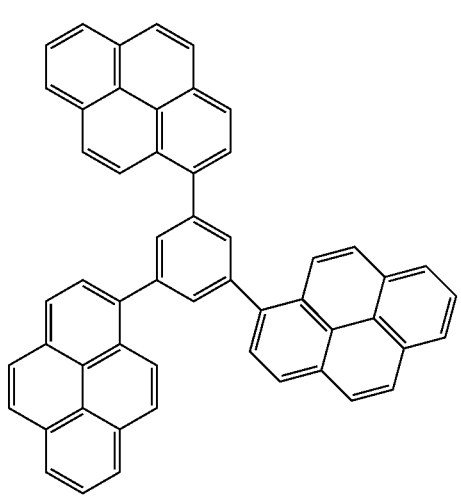

-continued
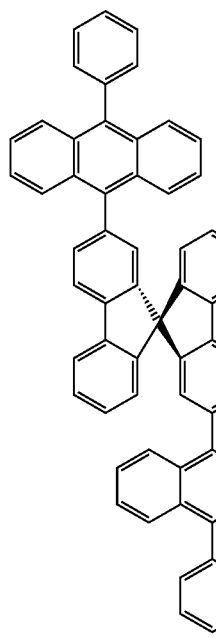
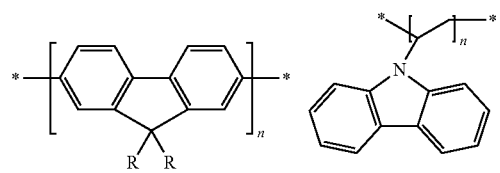
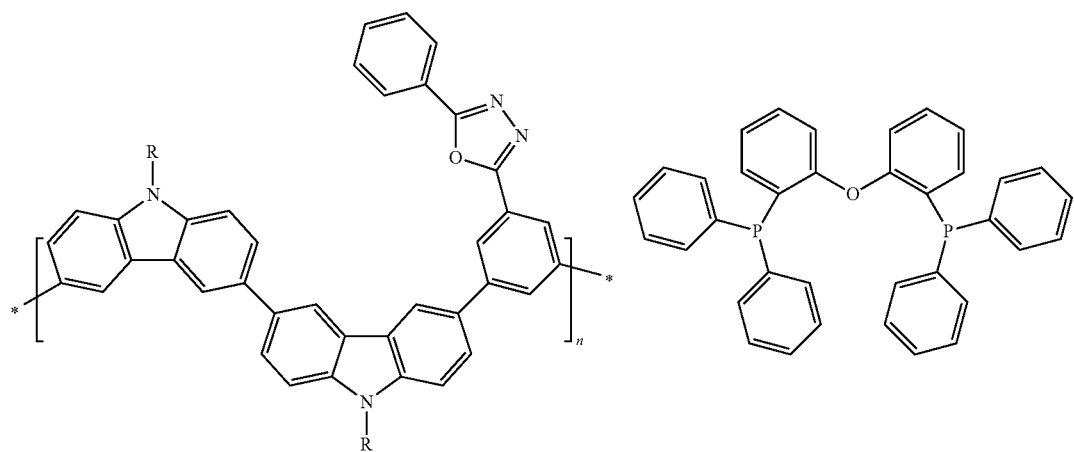
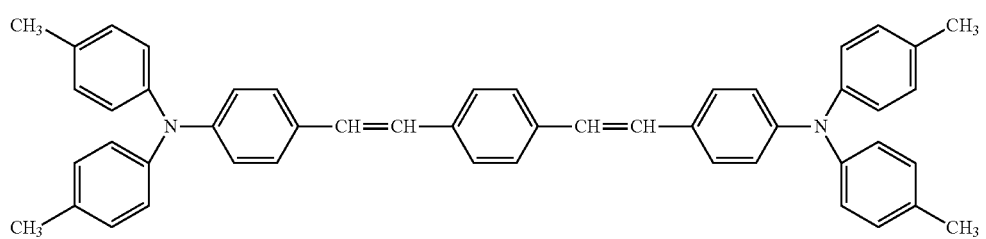
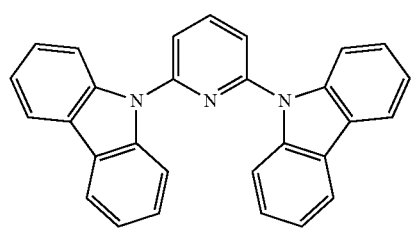

Preferred examples of a compound that may be used as the hole injection material are shown below.
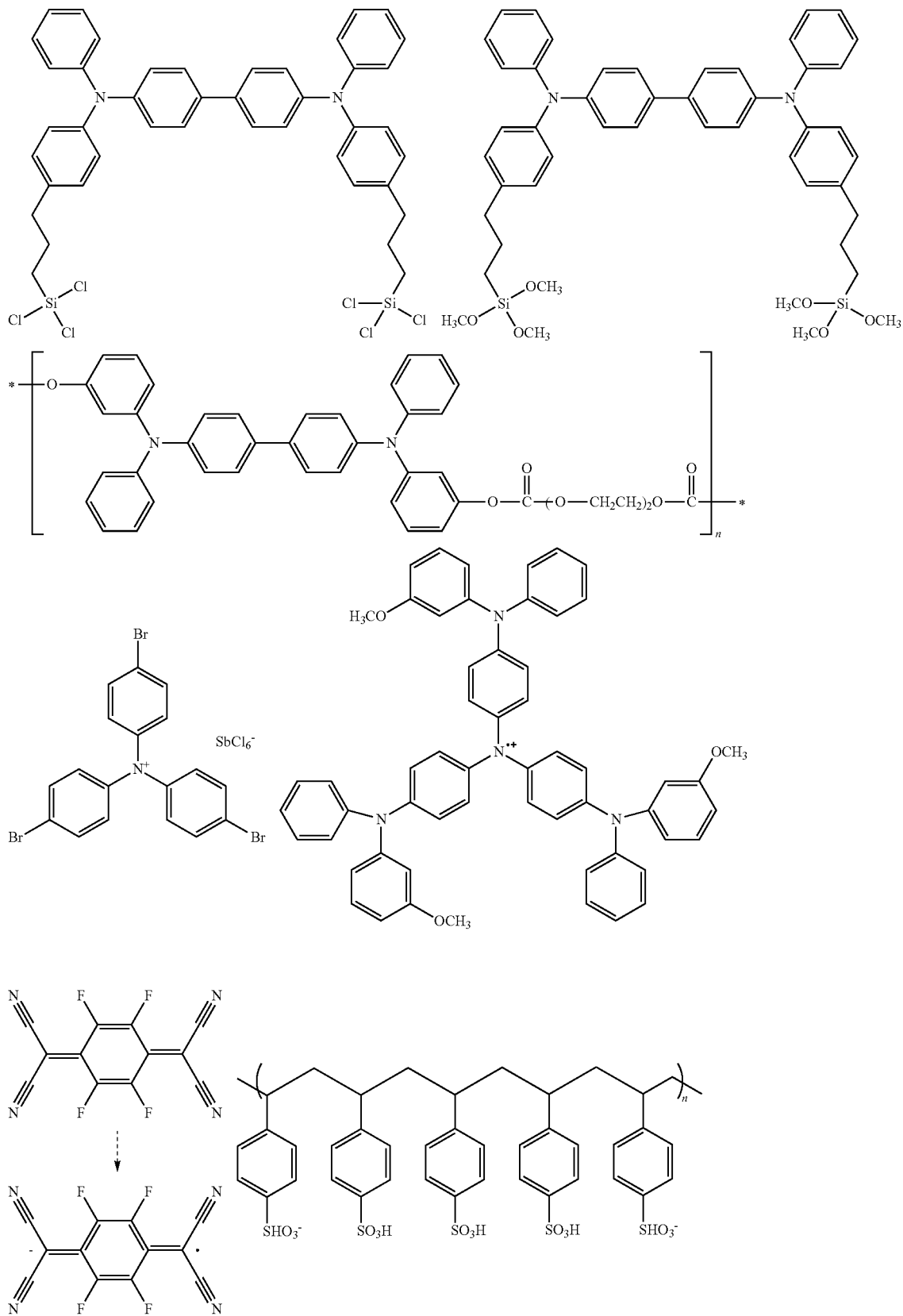

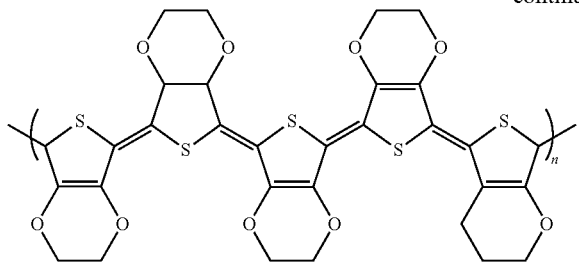
Preferred examples of a compound that may be used as the hole transporting material are shown below.
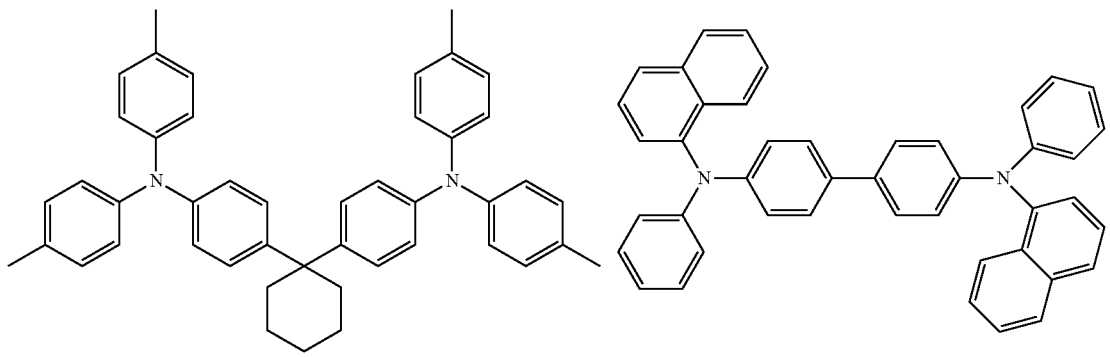
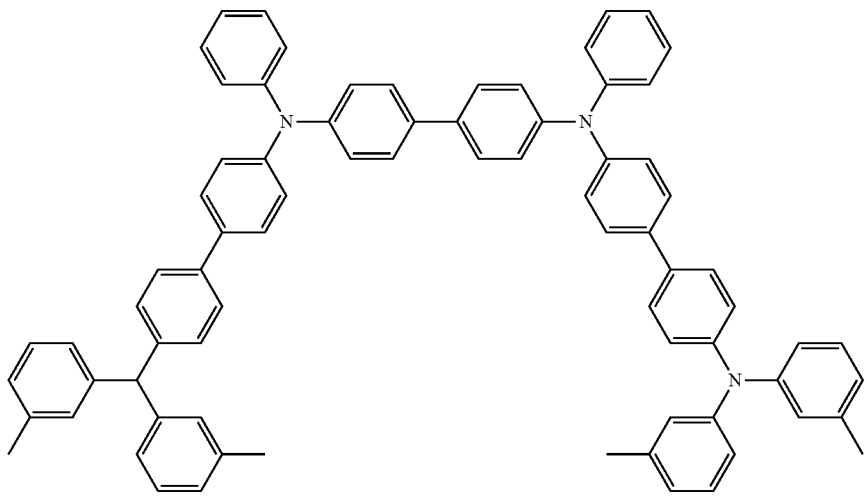
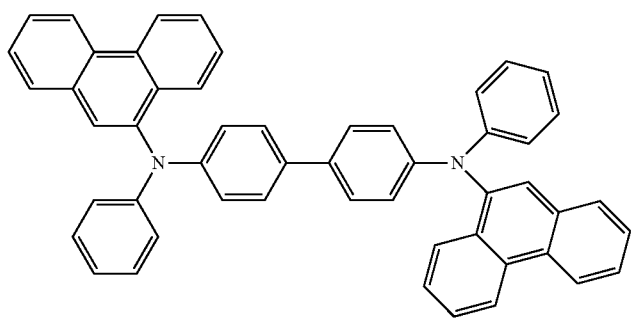

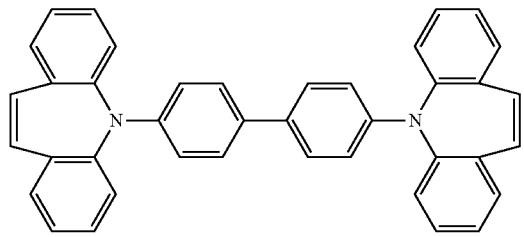
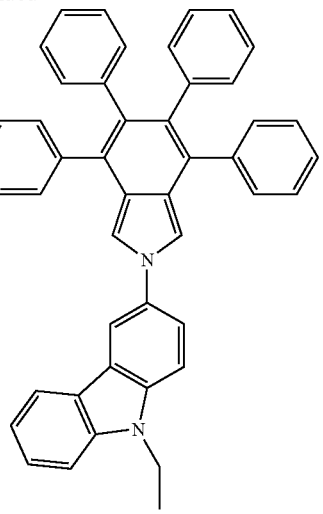
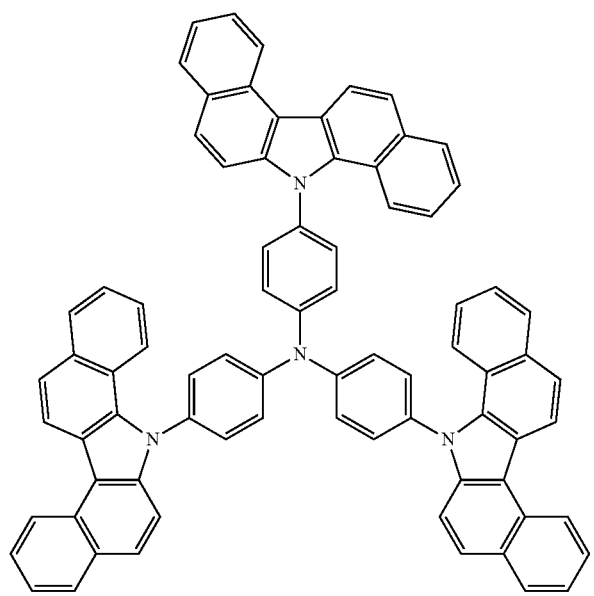
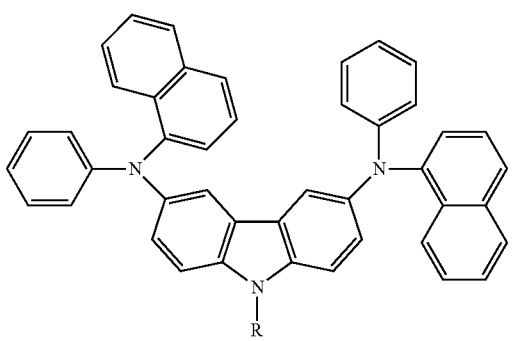
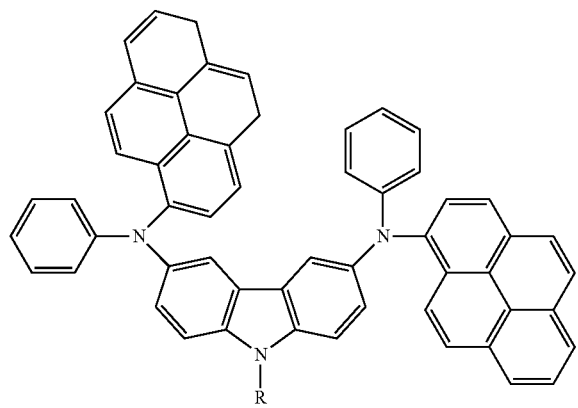

-continued
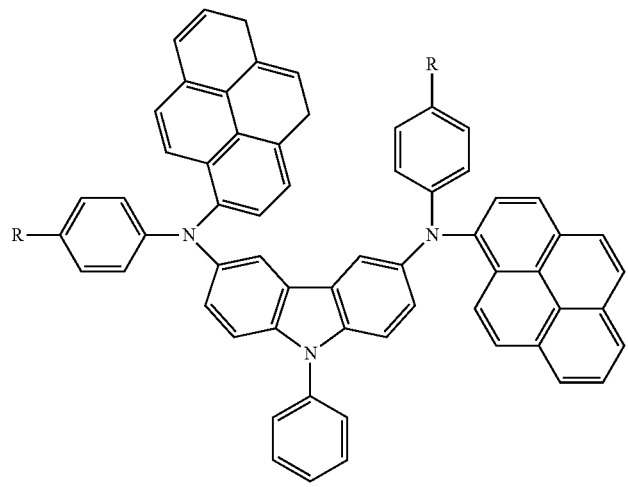
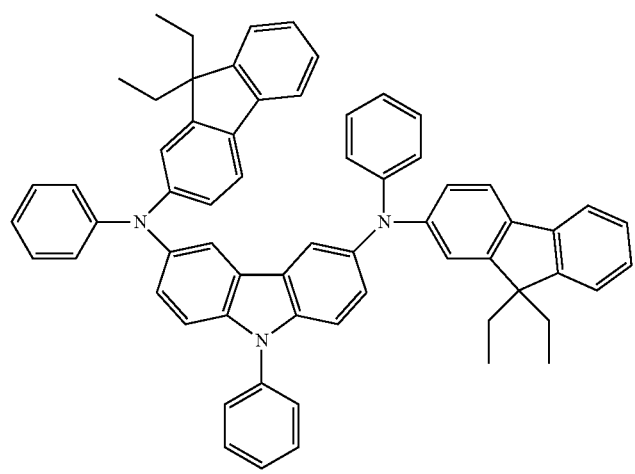
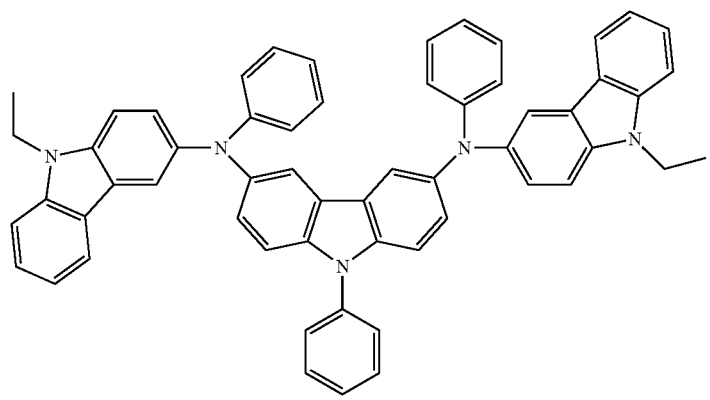

-continued
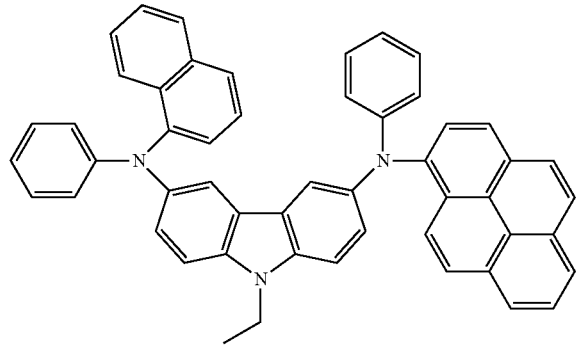
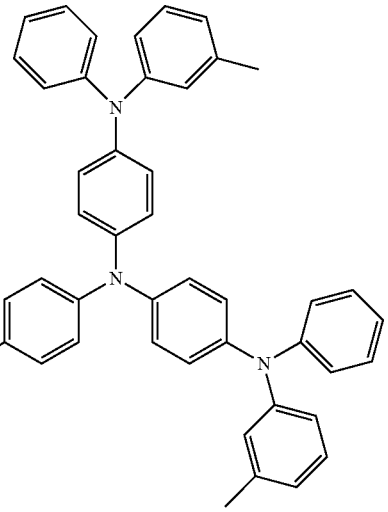
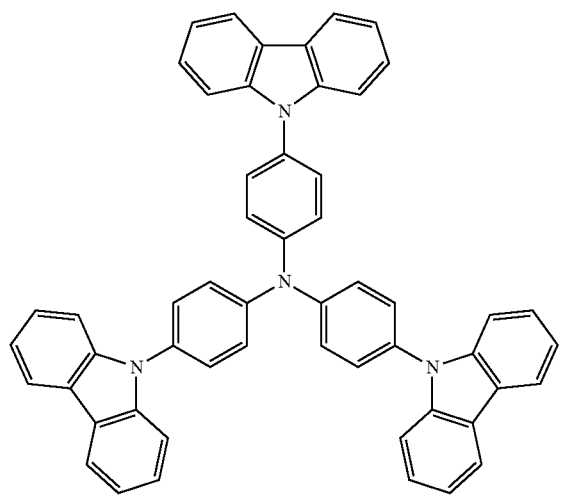
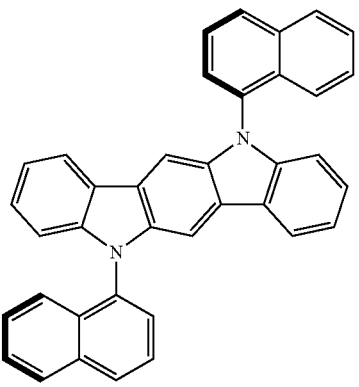
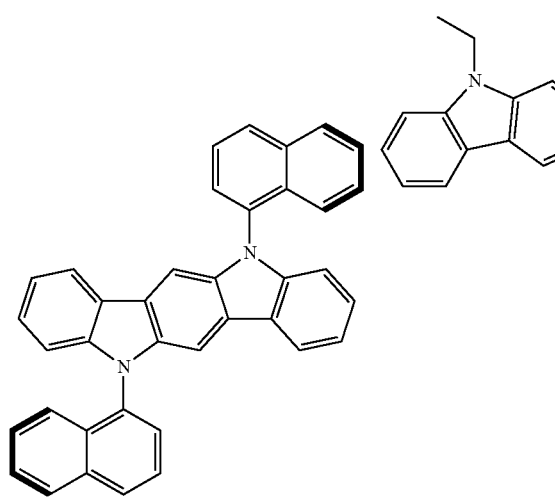
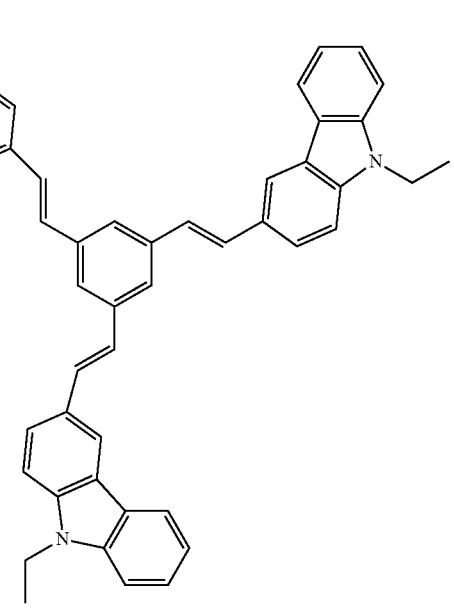

-continued
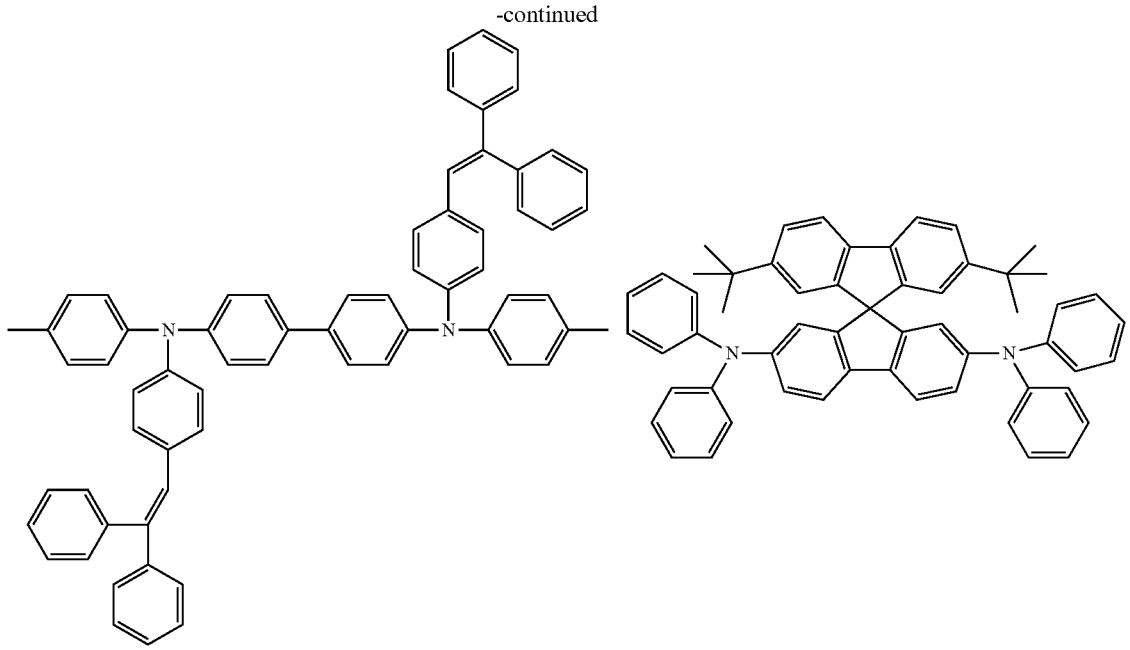
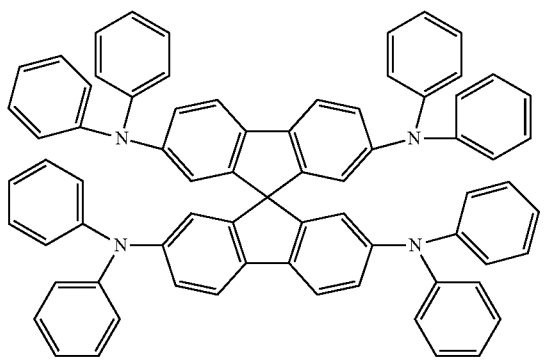
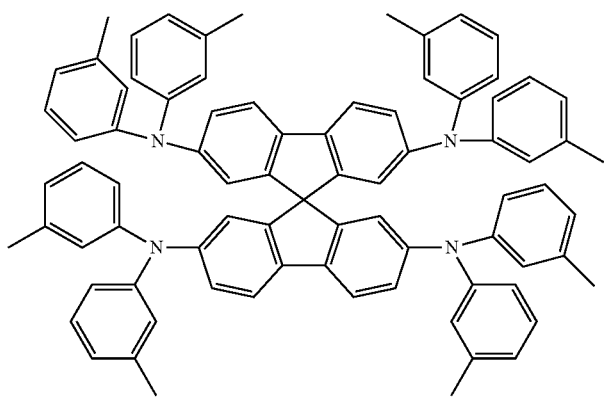

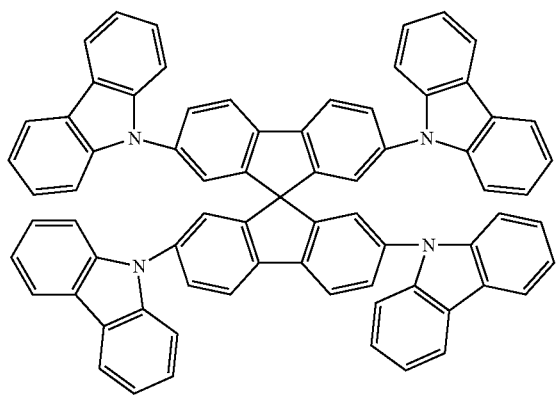
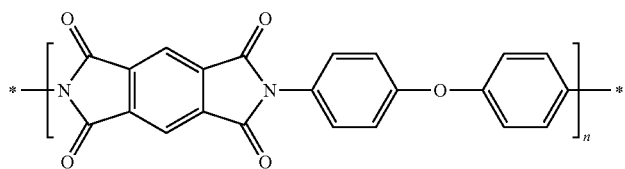
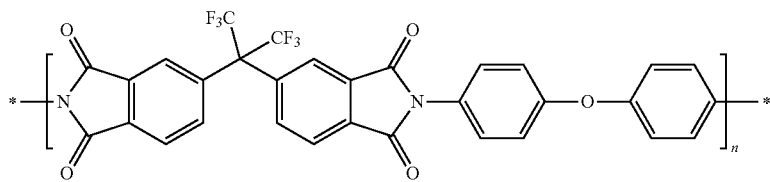
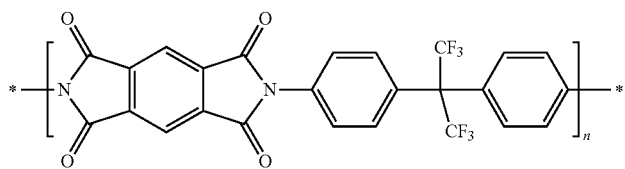
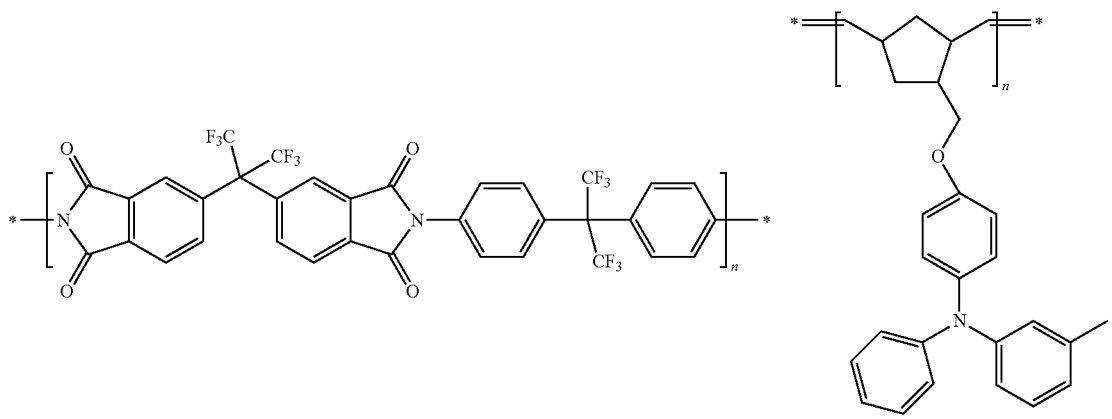

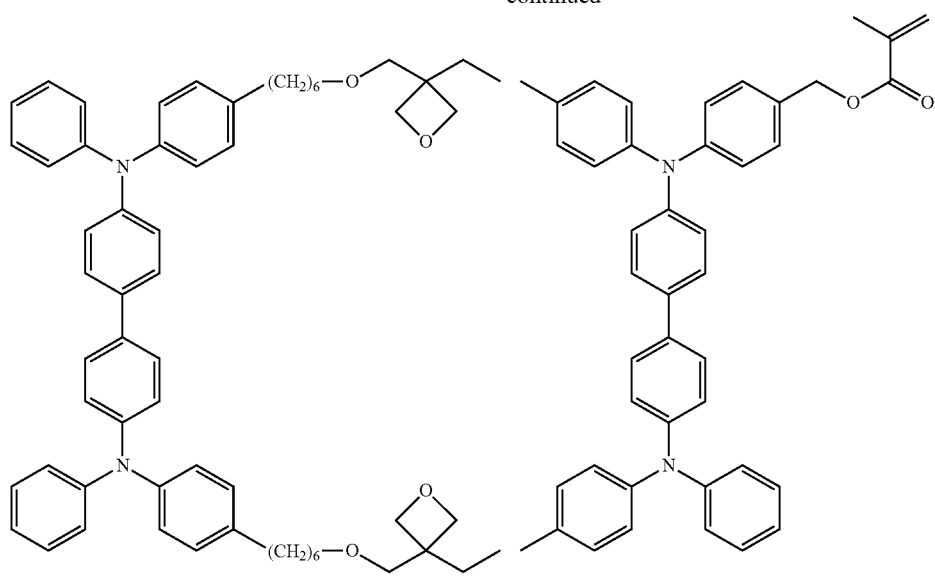
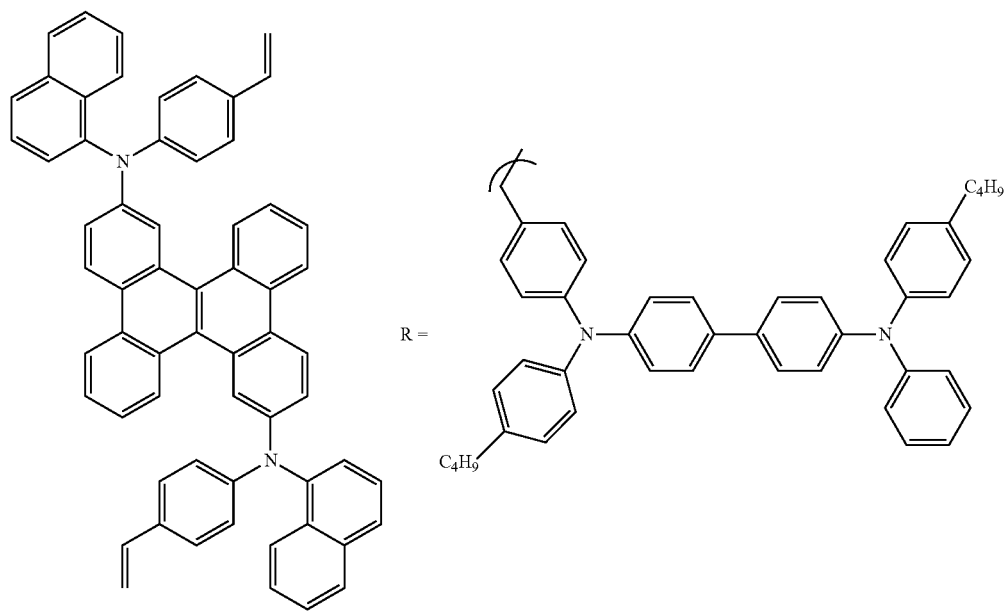
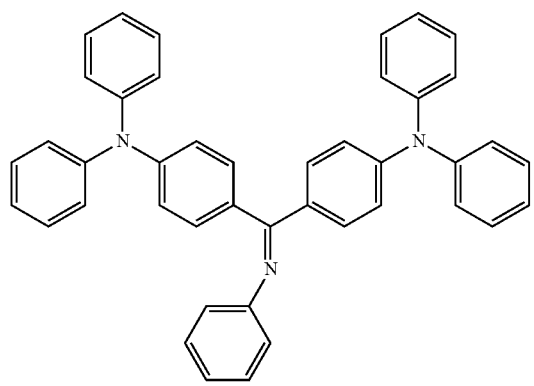

-continued
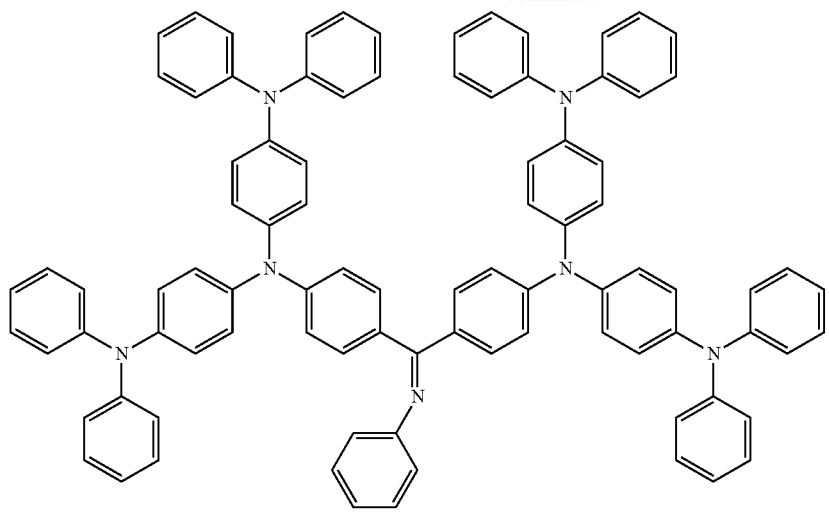
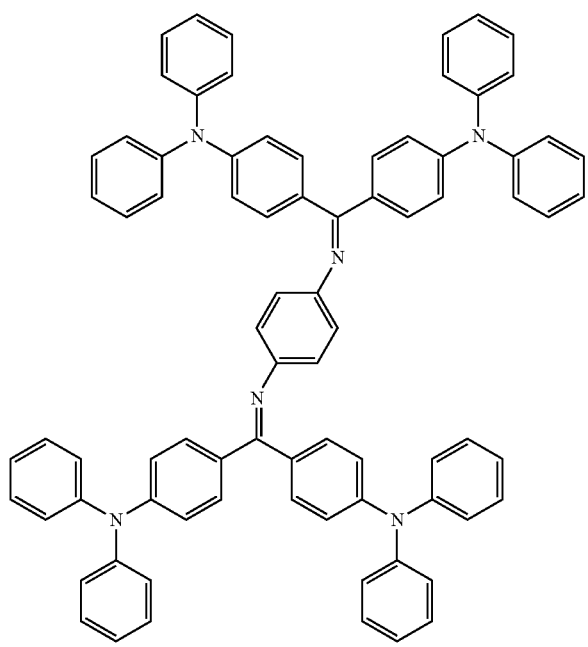

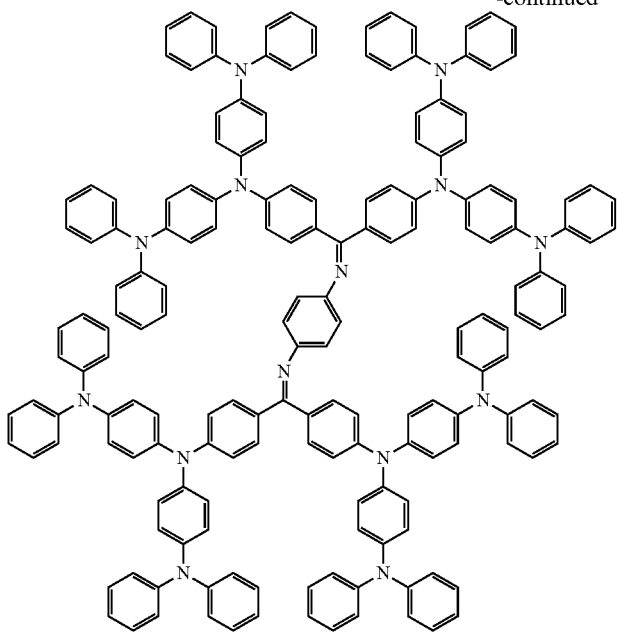
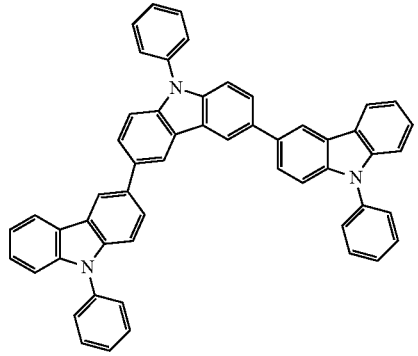
Preferred examples of a compound that may be used as the electron barrier material are shown below.
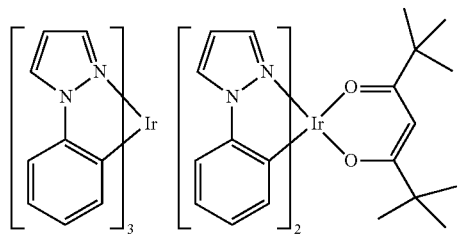
-continued
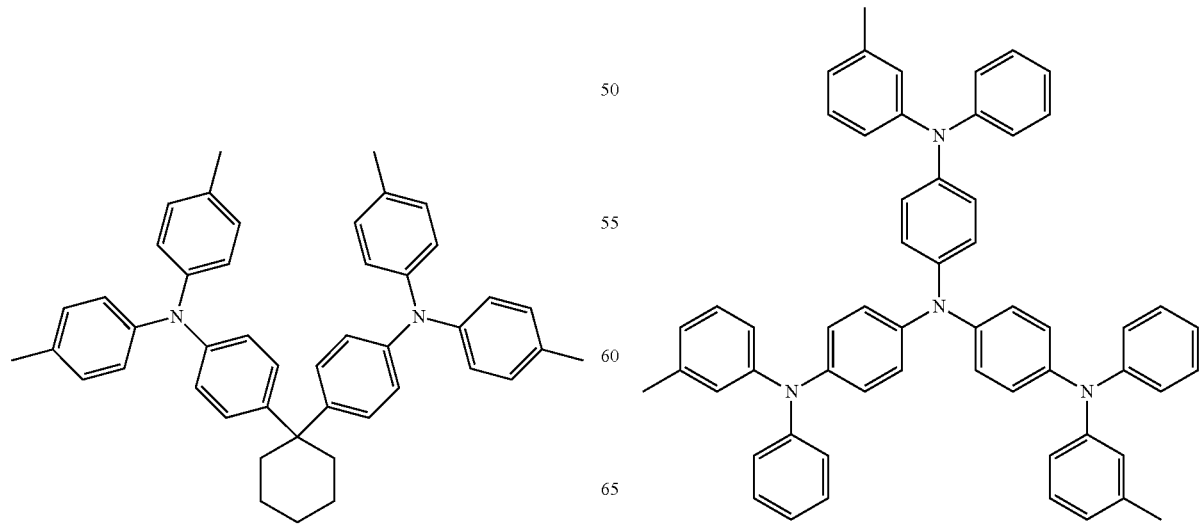

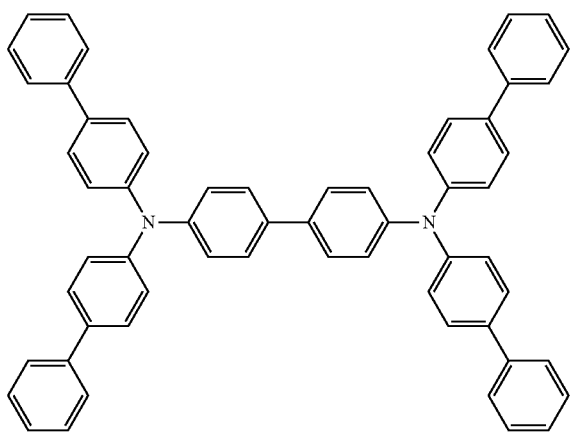 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
Preferred examples of a compound that may be used as the hole barrier material are shown below.
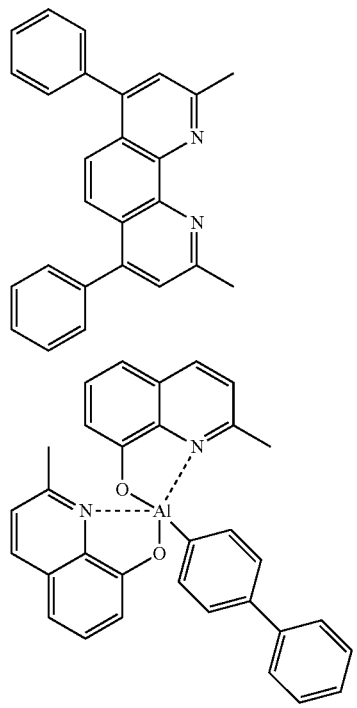
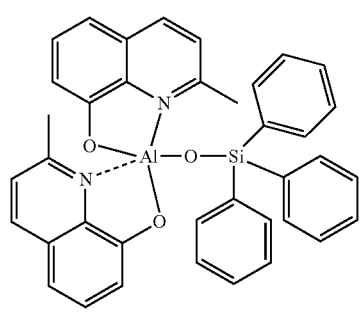
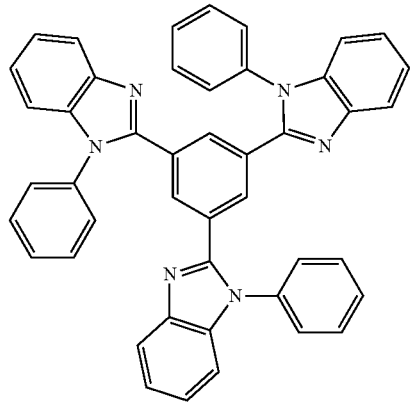
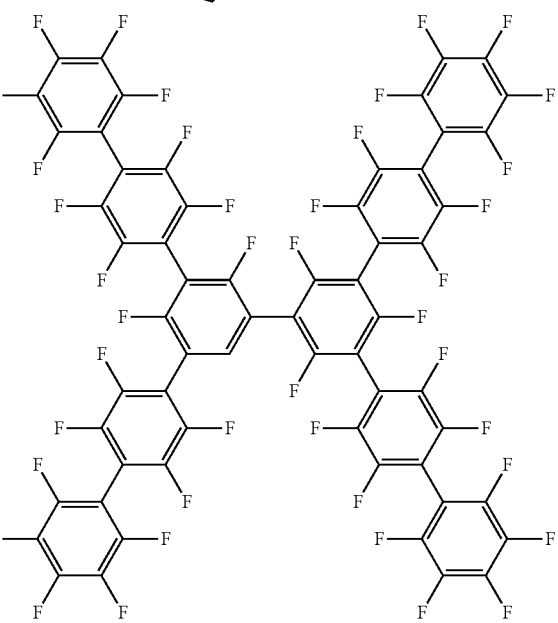
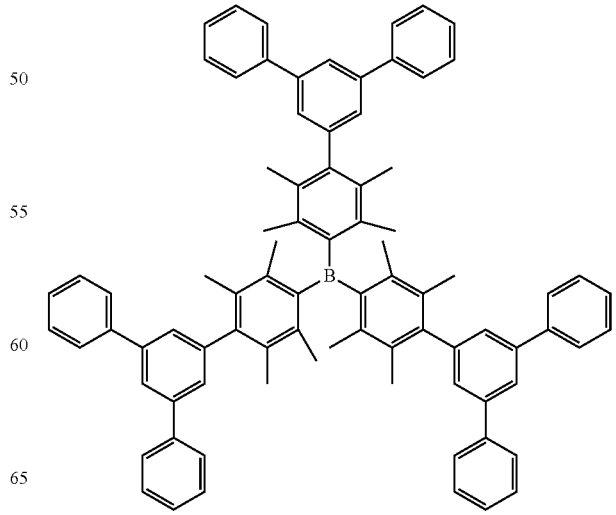

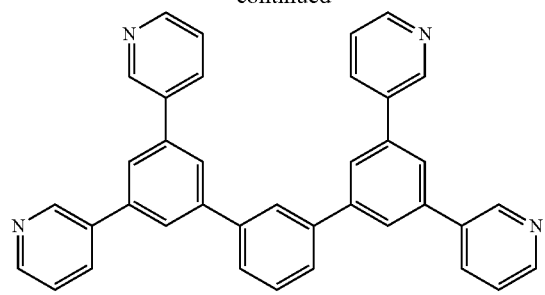
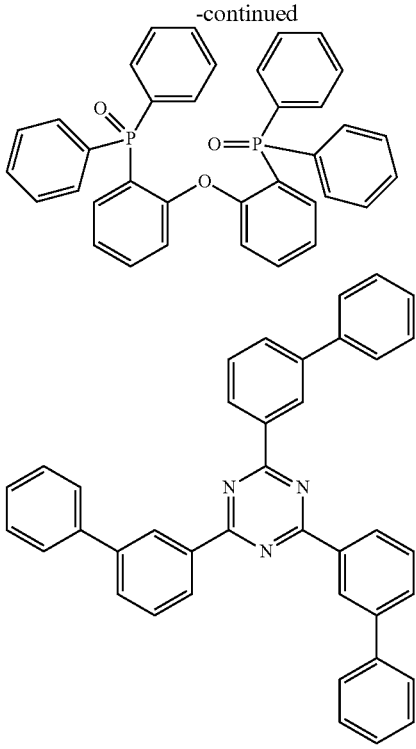
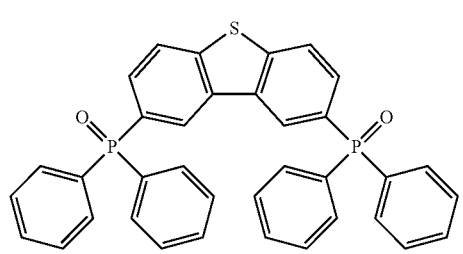
Preferred examples of a compound that may be used as the electron transporting material are shown below.
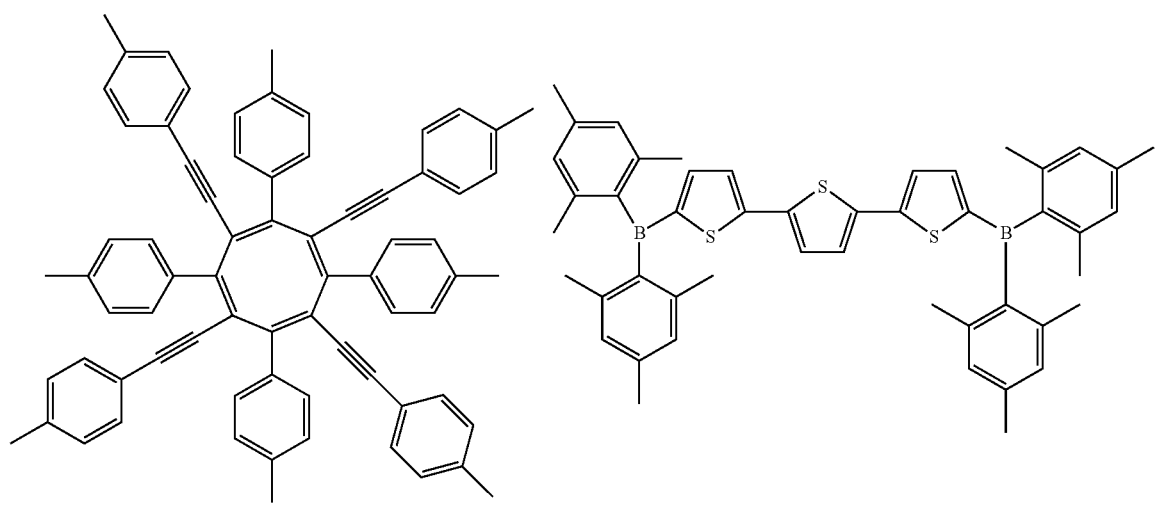
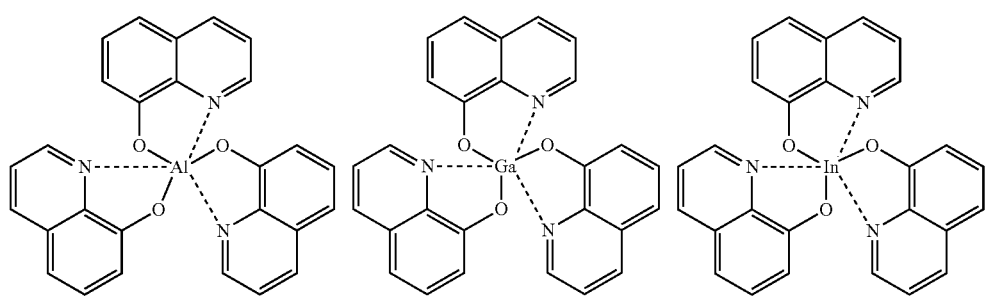

57
58
-continued
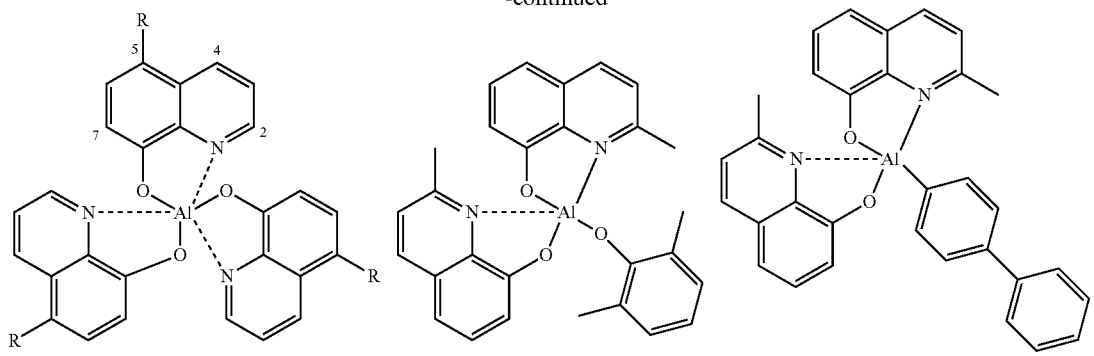
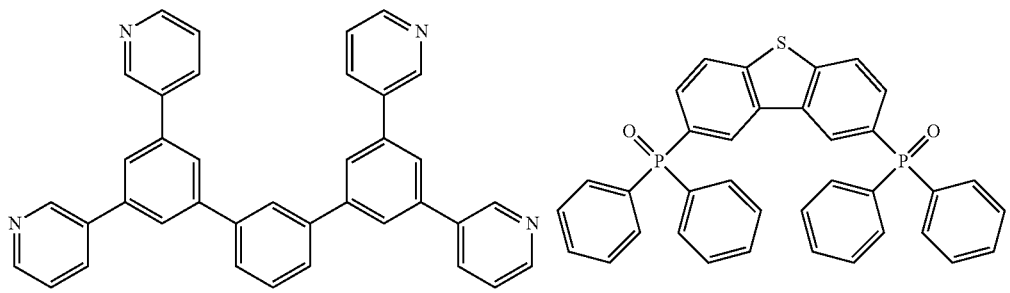
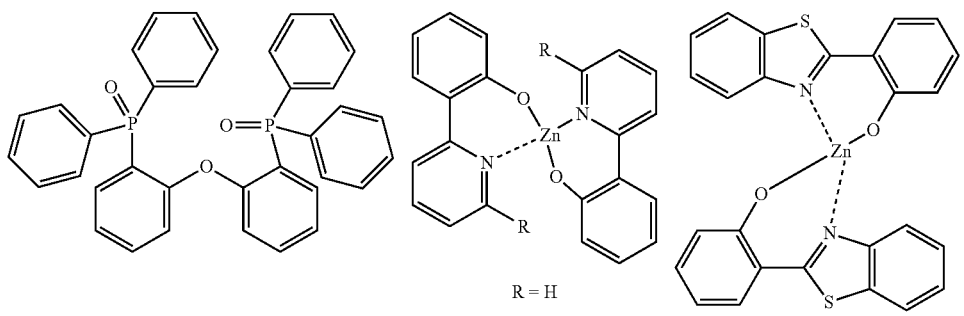
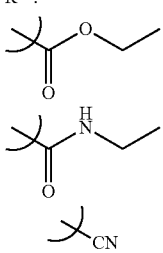
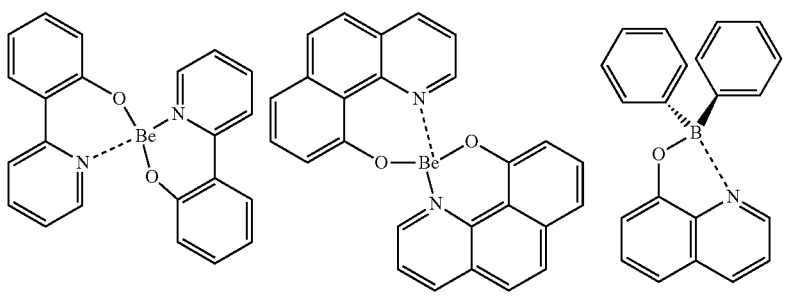

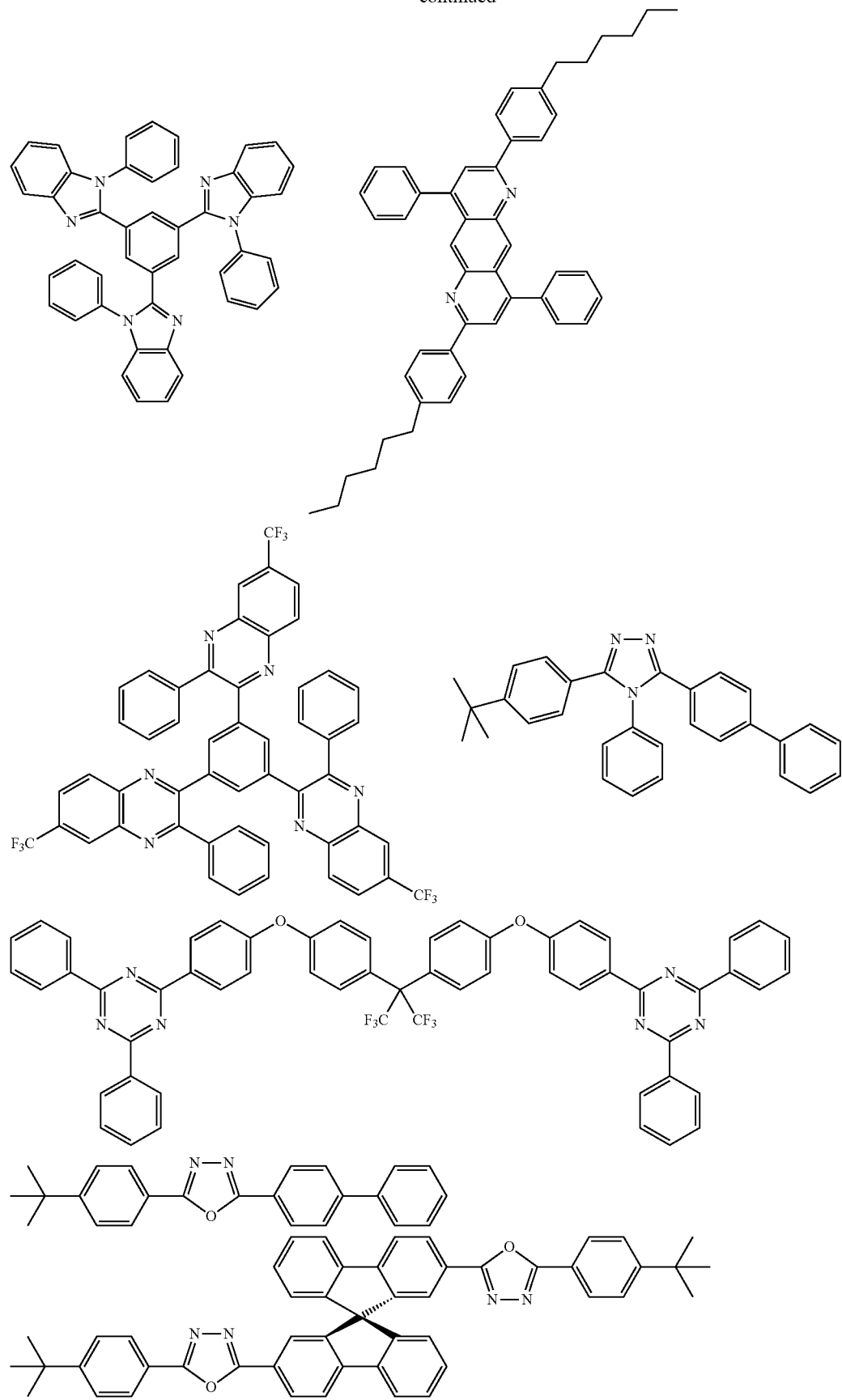

-continued
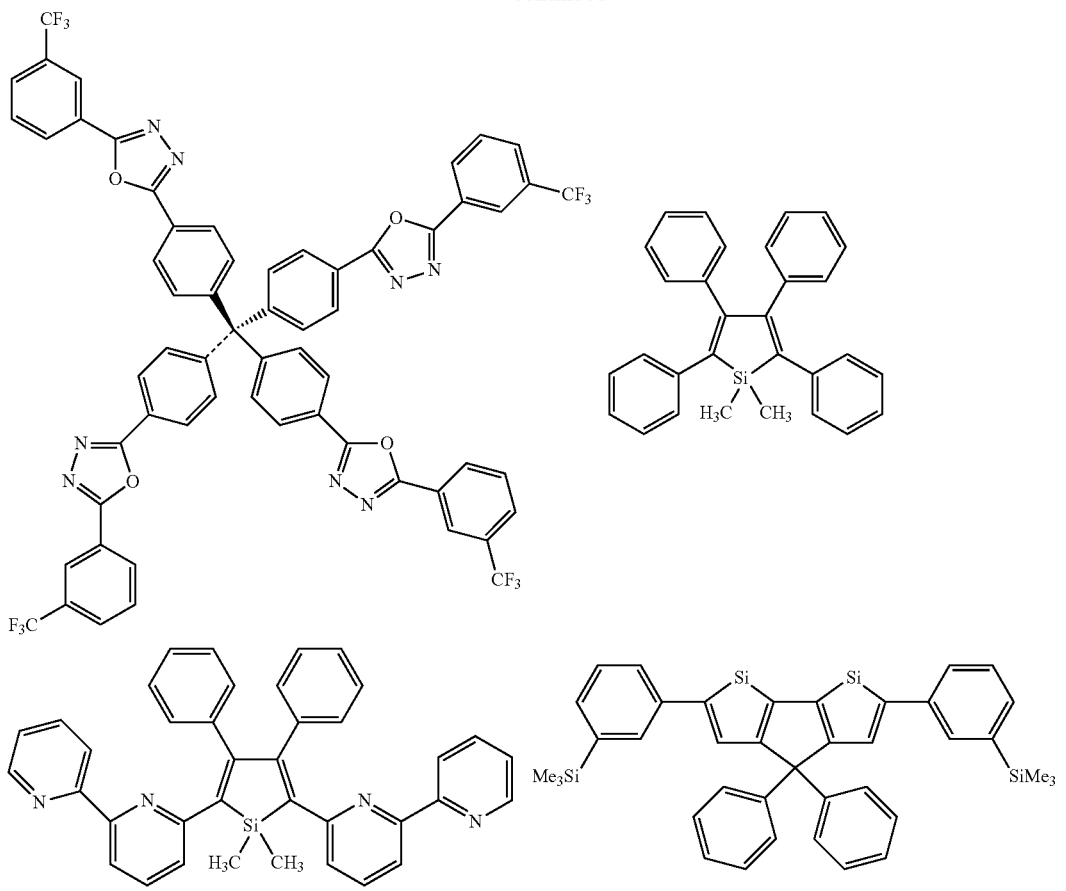
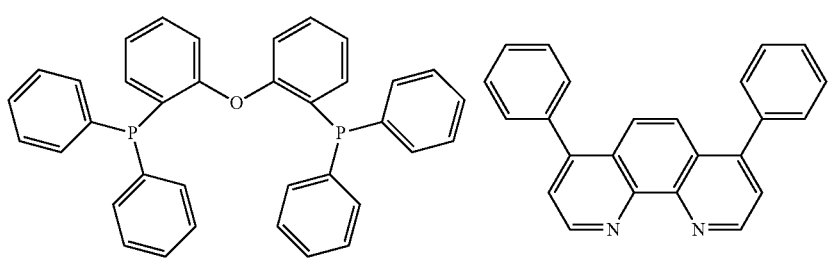
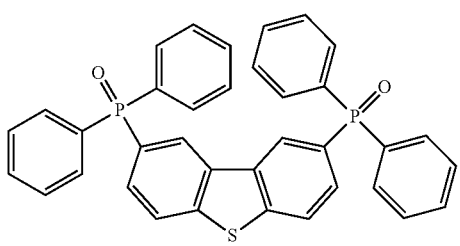

Preferred examples of a compound that may be used as the electron injection material are shown below.

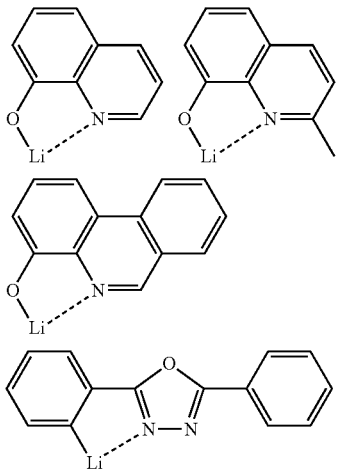

Preferred examples of a compound as a material that may be added are shown below. For example, the compound may be added as a stabilizing material.

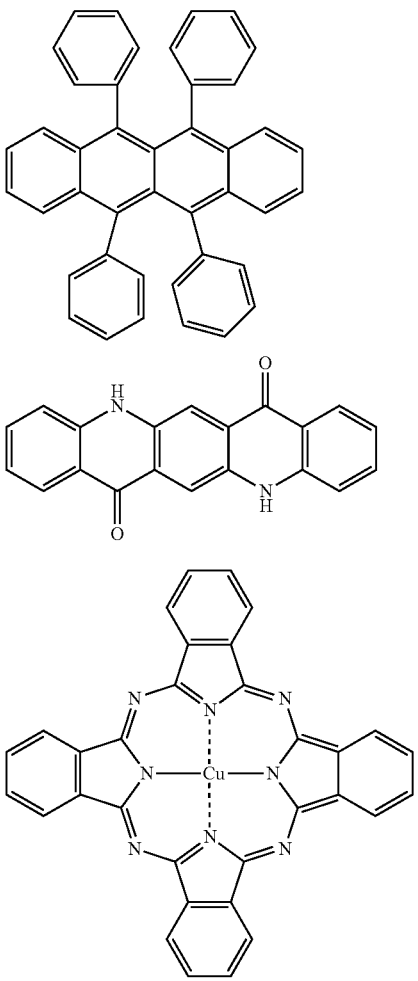

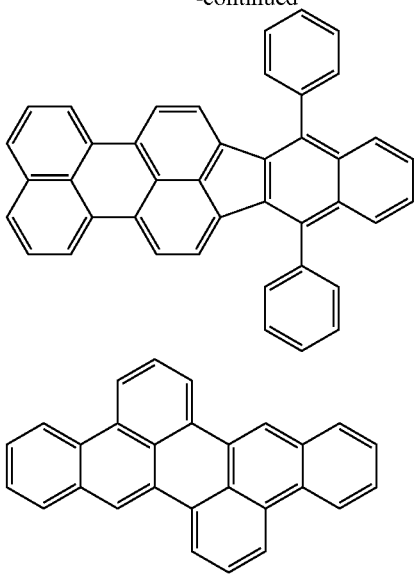

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light emitting device that is largely improved in light emission efficiency may be obtained by adding the compound represented by the general formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.) In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K. K).

Synthesis Example 1

Synthesis of Compound 1

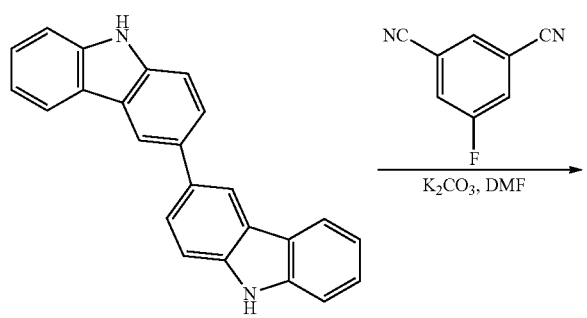

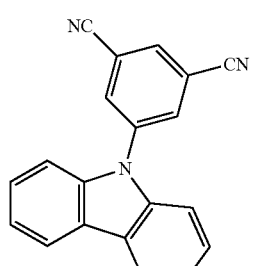

Compound 1

3.00 g (9.03 mmol) of 3,3'-bi-9H-carbazole and 4.98 g (36.0 mmol) of potassium carbonate were charged in a 200 mL three-neck flask, and the interior of the flask was substituted by nitrogen. 78.0 mL of N,N-dimethylformamide was added to the resulting mixture, which was then stirred at room temperature under a nitrogen stream for 2 hours. 2.93 g (18.0 mmol) of 5-fluoroisophthalonitrile was added to the mixture, which was then stirred at 70° C. under a nitrogen stream for 20 hours. After completing the stirring, the solvent was removed from the mixture through distillation under reduced pressure. After completing the removal, 100 mL of chloroform and 50 mL of water were added to the mixture, which was then stirred. After completing the stirring, the mixture was suction-filtered to provide a filtrate. The resulting filtrate was separated into an aqueous layer and an organic layer, and the organic layer was rinsed with water. After completing the rinsing, the organic layer was dried over magnesium sulfate added thereto. After completing the drying, the mixture was suction-filtered to provide a filtrate. The resulting filtrate was concentrated and purified by silica gel chromatography. The developing solvent used was a mixed solvent of chloroform and ethyl acetate (10/1) The resulting fraction was concentrated to provide a solid matter, which was then recrystallized from a mixed solvent of chloroform and methanol, so as to provide a pale orange powder solid matter as the target product in a yield amount of 0.700 g and a yield of 13.3%.

$^1$H NMR (500 MHz, CDCl$_3$, δ): 8.45 (d, J=1.5 Hz, 2H), 8.26 (d, J=7.8 Hz, 2H), 8.22 (d, 1.5 Hz, 4H), 8.02 (t, 1.4 Hz, 2H), 7.83 (dd, J=8.5 Hz, 1.8 Hz, 2H), 7.54-7.51 (m, 4H), 7.45-7.42 (m, 4H)

elemental analysis:
calculated (C$_{40}$H$_{20}$N$_6$): C 82.18; H 3.45; N 14.37%
measured: C 82.07; H 3.51; N 14.34%

Synthesis Example 2

Synthesis of Compound 2

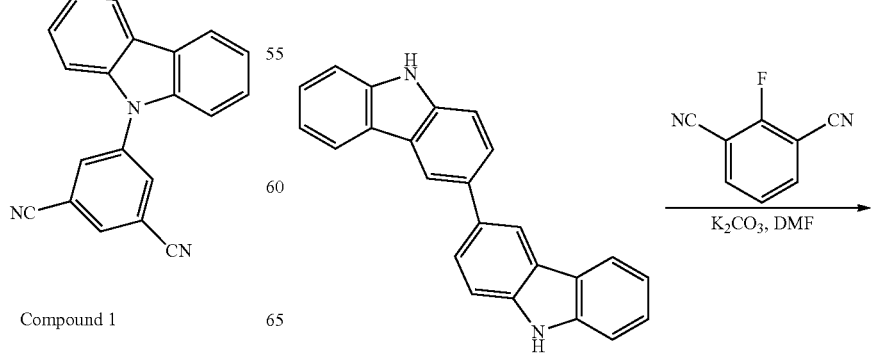

-continued

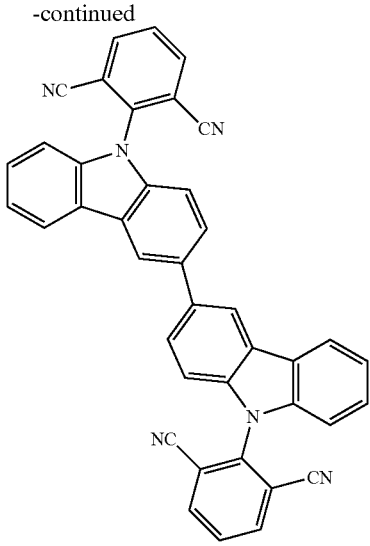

Compound 2

1.00 g (3.01 mmol) of 3,3'-bi-9H-carbazole and 1.66 g (12.0 mmol) of potassium carbonate were charged in a 100 mL three-neck flask, and the interior of the flask was substituted by nitrogen. 24.0 mL of N,N-dimethylformamide was added to the resulting mixture, which was then stirred at room temperature under a nitrogen stream for 2 hours. 1.80 g (11.1 mmol) of 2-chloroisophthalonitrile was added to the mixture, which was then stirred at 150° C. under a nitrogen stream for 20 hours. After completing the stirring, the solvent was removed from the mixture through distillation under reduced pressure. After completing the removal, 100 mL of ethyl acetate and 50 mL of water were added to the mixture, which was then stirred. After completing the stirring, the mixture was suction-filtered to provide a filtrate. The resulting filtrate was separated into an aqueous layer and an organic layer, and the organic layer was rinsed with water. After completing the rinsing, the organic layer was dried over magnesium sulfate added thereto. After completing the drying, the mixture was suction-filtered to provide a filtrate. The resulting filtrate was concentrated and purified by silica gel chromatography. The developing solvent used was a mixed solvent of acetone, ethyl acetate and hexane 1/5/5). The resulting fraction was concentrated to provide a solid matter, which was then recrystallized from a mixed solvent of chloroform and methanol, so as to provide a pale orange powder solid matter as the target product in a yield amount of 0.902 g and a yield of 51.3%.

$^1$H NMR (500 MHz, Acetone-d$_6$, δ): 8.70 (d, J=1.4 Hz, 2H), 8.53 (d, J=8.0 Hz, 4H), 8.42 (d, 7.7 Hz, 2H), 8.14 (t, 8.0 Hz, 2H), 7.93 (dd, J=8.5 Hz, 1.8 Hz, 2H), 7.52 (t, J=7.5 Hz, 2H), 7.44-7.41 (m, 4H), 7.30 (d, 8.2 Hz, 2H)

$^{13}$C NMR (125 MHz, Acetone-d$_6$, δ): 143.30, 142.06, 140.83, 139.97, 136.28, 131.75, 127.70, 127.27, 125.60, 125.12, 122.33, 121.90, 120.41, 116.46, 115.26, 110.97, 110.75 elemental analysis:
calculated ($C_{40}H_{20}N_6$): C 82.18; H 3.45; N 14.37%
measured: C 82.23; H 3.52; N 14.39%

Example 1

Production and Evaluation of Thin Film Organic Photoluminescent Device

The compound 1 and DPEPO were vapor-deposited from separate vapor deposition sources on a quartz substrate by a vacuum vapor deposition method under a condition of a vacuum degree of $10^{-4}$ Pa or less to form a thin film having a thickness of 100 nm having a concentration of the compound 1 of 10% by weight, thereby completing a thin film organic photoluminescent device.

A thin film organic photoluminescent device using the compound 2 instead of the compound 1 was also produced.

Figure 2:
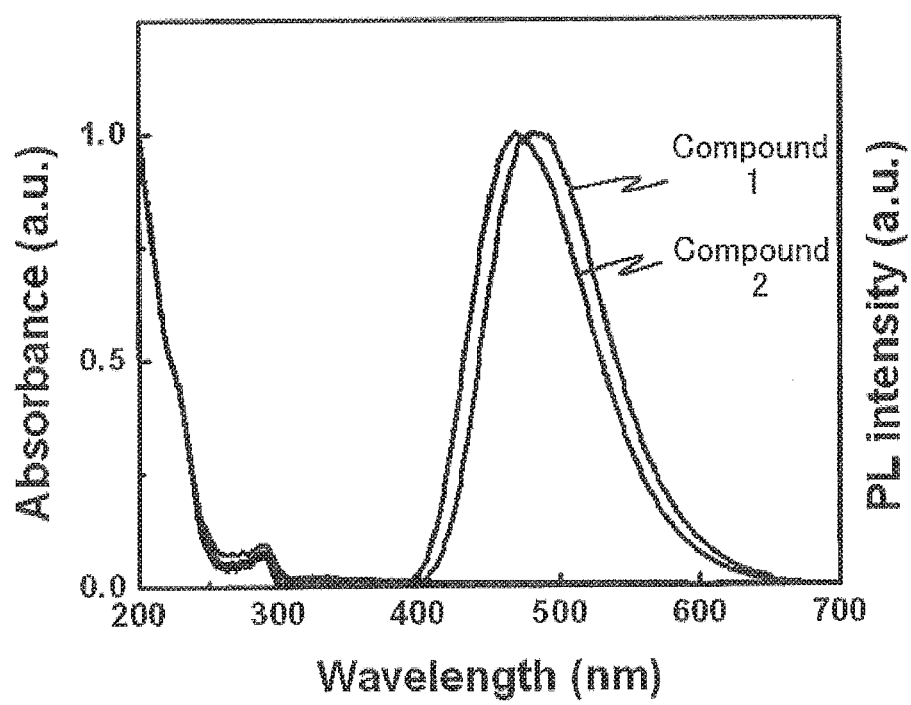
FIG. 2 is the light emission spectra of the thin film organic photoluminescent devices in Example 1.

FIG. 2 shows the light emission spectra of the thin film organic photoluminescent devices.

Figure 3:
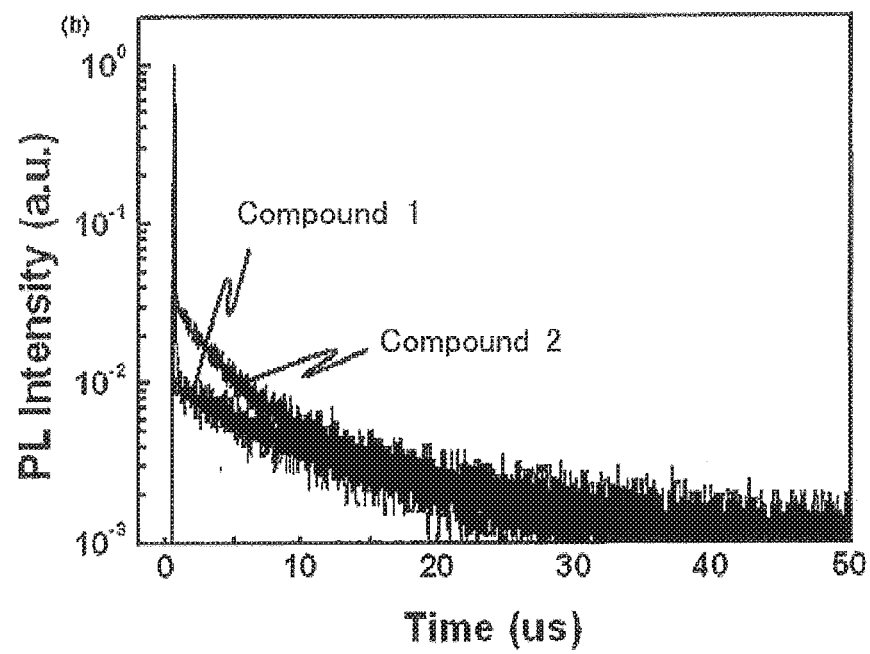
FIG. 3 is the transient decay curves of the thin film organic photoluminescent devices in Example 1.

FIG. 3 shows the transient decay curves of the thin film organic photoluminescent device using the compound 1 and the thin film organic photoluminescent device using the compound 2. The transient decay curves each show the measurement result of the light emission lifetime in the process of deactivating the light emission intensity starting from the irradiation of the compound with excitation light. In the ordinary one-component light emission (fluorescent light or phosphorescent light), the light emission intensity decays monoexponentially. This means the linear decay in the case where the ordinate of the graph is in a semilogarithmic scale. In the transient decay curve of the compound 1 shown in FIG. 3, the linear component (fluorescent light) is observed in the initial stage of observation, but a component that deviates from the liniarity appears after several microseconds. This is the light emission of the delayed component, and the signal obtained by adding the initial component forms a gentle curve having a long tail on the long time side. Thus, the measurement of the light emission lifetime confirmed that the compound 1 was a light emitting material that exhibited a delayed component in addition to a fluorescent component.

Example 2

Production and Evaluation of Organic Electroluminescent Device

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 30 nm on ITO, and then mPC was formed to a thickness of 10 nm thereon. Subsequently, the compound 1 and DPEPO were co-deposited thereon from separate vapor deposition sources to form a layer having a thickness of 20 nm, which was designated as a light emitting layer. At this time, the concentration of the compound 1 was 10% by weight. DPEPO was then formed to a thickness of 10 nm, TPBi was formed to a thickness of 30 nm, further lithium fluoride (LiF) was vacuum vapor-deposited to a thickness of 0.5 nm, and then aluminum (Al) was vapor-deposited to a thickness of 100 nm to form a cathode, thereby completing an organic electroluminescent device.

An organic electroluminescent device using the compound 2 instead of the compound 1 was also produced.

Figure 4:
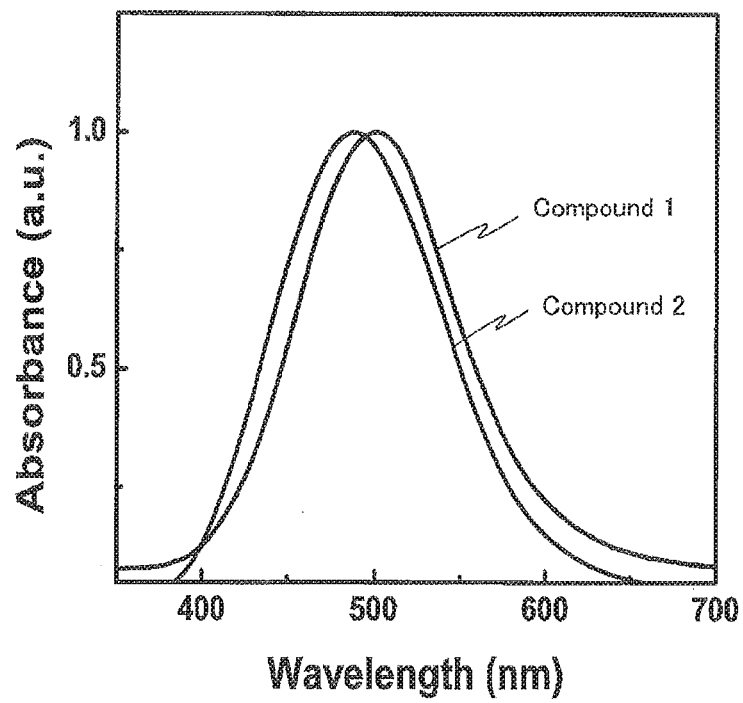
FIG. 4 is the light emission spectra of the organic electroluminescent devices in Example 2.

FIG. 4 shows the light emission spectra of the organic electroluminescent devices.

Figure 5:
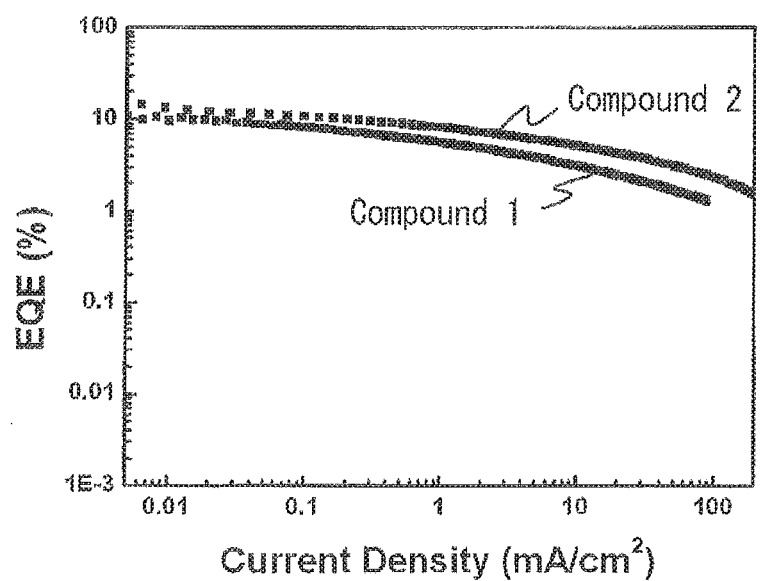
FIG. 5 is the electric current density-external quantum efficiency characteristics of the organic electroluminescent devices in Example 2.

FIG. 5 shows the electric current density-external quantum efficiency characteristics of the organic electroluminescent device using the compound 1 and the organic electroluminescent device using the compound 2. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value or an external quantum efficiency of an organic electroluminescent device using a fluorescent material. As apparent from FIG. 5, the organic electroluminescent device of the invention using the compound 1 is considerably excellent in such a point that a high external quantum efficiency that exceeds the theoretical limit value is achieved.

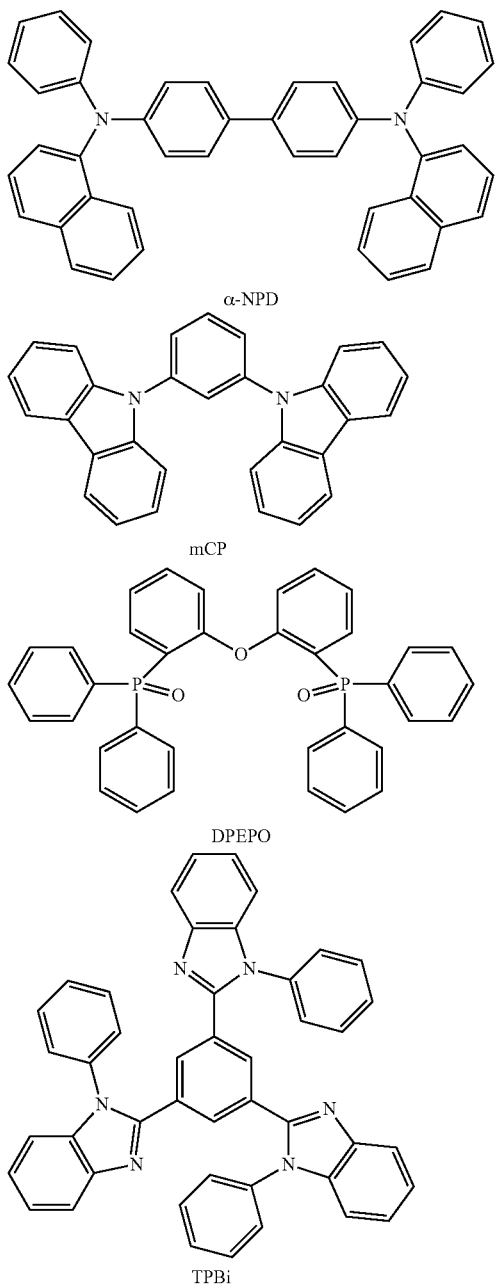

α-NPD mCP

DPEPO

TPBi

INDUSTRIAL APPLICABILITY

The compound of the invention is useful as a light emitting Accordingly, the compound of the invention may be effectively used as a light emitting material of an organic light emitting device, such as an organic electroluminescent device. The compound of the invention includes a compound that emits delayed fluorescent light, and thus may be capable of providing an organic light emitting device having a high light emission efficiency. Thus, the invention has high industrial applicability.

REFERENCE SIGNS LIST 1 substrate
2 anode
3 hole injection layer
4 hole transporting layer
5 light emitting layer
6 electron transporting layer
7 cathode

The invention claimed is:

1. A compound represented by the following general formula (2):

General Formula (2)

wherein in the general formula (2), $R^1$ to $R^5$ each independently represent a hydrogen atom, a cyano group or an alkyl group having from 1 to 10 carbon atoms, provided that $R^2$ and at least one of $R^1$, $R^4$ and $R^5$ represent a cyano group; $R^6$ to $R^{10}$ each independently represent a hydrogen atom, a cyano group or an alkyl group having from 1 to 10 carbon atoms, provided that at least $R^7$ and two of $R^6$, $R^9$ and $R^{10}$ represents a cyano group; and $R^{11}$ to $R^{17}$ and $R^{21}$ to $R^{27}$ each independently represent a hydrogen atom or an alkyl group having from 1 to 10 carbon atoms.

2. The compound according to claim 1, wherein the two cyanobenzenes bonded to the nitrogen atoms of the carbazole rings in the general formula (2) have the same structure.

3. The compound according to claim 1, wherein in the general formula (2), $R^2$, $R^4$, $R^7$ and $R^9$ each represent a cyano group.

4. The compound according to claim 1, wherein in the general formula (2), $R^1$ to $R^5$ and $R^6$ to $R^{10}$ except for those representing a cyano group each represent a hydrogen atom, and $R^{11}$ to $R^{17}$ and $R^{21}$ to $R^{27}$ each represent a hydrogen atom.

5. A light emitting material comprising the compound according to claim 1.

6. A compound represented by the following general formula (2):

General Formula (2)

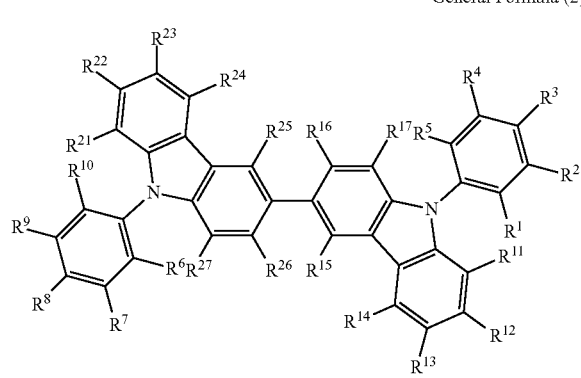

wherein in the general formula (2), $R^1$ to $R^5$ each independently represent a hydrogen atom, a cyano group or an alkyl group having from 1 to 10 carbon atoms, provided that $R^1$ and at least one of $R^2$, $R^4$ and $R^5$ represent a cyano group; $R^6$ to $R^{10}$ each independently represent a hydrogen atom, a cyano group or an alkyl group having from 1 to 10 carbon atoms, provided that at least two of $R^6$, $R^7$, $R^9$ and $R^{10}$ represents a cyano group; and $R^{11}$ to $R^{17}$ and $R^{21}$ to $R^{27}$ each independently represent a hydrogen atom or an alkyl group having from 1 to 10 carbon atoms.

7. The compound according to claim 6, wherein in the general formula (2), $R^1$, $R^5$, $R^6$ and $R^{10}$ each represent a cyano group.

8. An organic light emitting device comprising a substrate having thereon a light emitting layer containing the light emitting material according to claim 5 as a light emitting material.

9. The organic light emitting device according to claim 8, wherein the organic light emitting device emits delayed fluorescent light.

10. The organic light emitting device according to claim 8, wherein the organic light emitting device is an organic electroluminescent device.

* * * * *